US012196679B2

(12) United States Patent
Cutrale et al.

(10) Patent No.: US 12,196,679 B2
(45) Date of Patent: Jan. 14, 2025

(54) HIGH THROUGHPUT SNAPSHOT SPECTRAL ENCODING DEVICE FOR FLUORESCENCE SPECTRAL MICROSCOPY

(71) Applicant: University of Southern California, Los Angeles, CA (US)

(72) Inventors: Francesco Cutrale, Los Angeles, CA (US); Pu Wang, Los Angeles, CA (US); Scott E. Fraser, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 191 days.

(21) Appl. No.: 17/911,006

(22) PCT Filed: Mar. 12, 2021

(86) PCT No.: PCT/US2021/022232
§ 371 (c)(1),
(2) Date: Sep. 12, 2022

(87) PCT Pub. No.: WO2021/183967
PCT Pub. Date: Sep. 16, 2021

(65) Prior Publication Data
US 2023/0092749 A1    Mar. 23, 2023

Related U.S. Application Data

(60) Provisional application No. 62/989,493, filed on Mar. 13, 2020.

(51) Int. Cl.
*G01N 21/64*   (2006.01)
*G02B 21/16*   (2006.01)
*G02B 21/36*   (2006.01)

(52) U.S. Cl.
CPC ..... *G01N 21/6458* (2013.01); *G01N 21/6428* (2013.01); *G02B 21/16* (2013.01);
(Continued)

(58) Field of Classification Search
CPC .......... G01N 21/6458; G01N 21/6428; G01N 2021/6417; G01N 2021/6439;
(Continued)

(56) References Cited

U.S. PATENT DOCUMENTS 5,117,466 A    5/1992   Buican
5,296,703 A    3/1994   Tsien
(Continued)

FOREIGN PATENT DOCUMENTS

WO    2018089383 A1    5/2018
WO    2020047594 A1    3/2020
WO    2021183967 A1    9/2021

OTHER PUBLICATIONS

International Search Report and Written Opinion for PCT/US2021/022232 dated Jun. 9, 2021, 11 pages.
(Continued)

*Primary Examiner* — Courtney D Thomas
(74) *Attorney, Agent, or Firm* — Linda B. Huber; Nixon Peabody LLP

(57) ABSTRACT

Systems and methods are provided for multi-spectral or hyper-spectral fluorescence imaging. In one example, a spectral encoding device may be positioned in a detection light path between a detection objective and an imaging sensor of a microscope. In one example, the spectral encoding device includes a first dichroic mirror having a sine transmittance profile and a second dichroic mirror having a cosine transmittance profile. In addition to collecting transmitted light, reflected light from each dichroic mirror is collected and used for total intensity normalization and image analysis.

30 Claims, 16 Drawing Sheets

Specification includes a Sequence Listing.

(52) U.S. Cl.
CPC ... *G02B 21/365* (2013.01); *G01N 2021/6417* (2013.01); *G01N 2021/6439* (2013.01); *G01N 2201/0636* (2013.01)

(58) Field of Classification Search
CPC ............ G01N 2201/0636; G02B 21/16; G02B 21/365; G02B 21/367; A61B 2576/00; A61B 5/0071; A61B 5/0075
See application file for complete search history.

(56) References Cited

U.S. PATENT DOCUMENTS

| | | | |
|---|---|---|---|
| 2010/0079857 A1* | 4/2010 | Sasaki | G02B 21/16 359/388 |
| 2018/0052313 A1 | 2/2018 | Hamilton et al. | |
| 2018/0259318 A1 | 9/2018 | Yelin et al. | |
| 2020/0378830 A1* | 12/2020 | Gratton | G01J 3/4406 |

OTHER PUBLICATIONS

IPRP for PCT/US2021/022232 dated Sep. 6, 2022, 10 pages.
Extended European Search Report, Application 21767543.8; issued Apr. 4, 2024, 11 pages.
"Hyperspectral imaging in highly scattering media by the spectral phasor approach using two filters," Dvornikov, Alexander et al.; Biomedical Optics Express, vol. 9, No. 8, Aug. 1, 2018, p. 3503, XP093141364, United States ISSN: 2156-7085, DOI: 1-.1364/BOE.9.003503.

* cited by examiner

| Acquisition Device 297 \ Fluorophore 296 | CFP | eGFP | eYFP | mCherry | iRFP670 |
|---|---|---|---|---|---|
| Sequential filter | 48.7% | 40.7% | 29.3% | 28.3% | 55.6% |
| Spectral encoding Device | 80.0% | 80.5% | 79.1% | 80.9% | 78.7% |

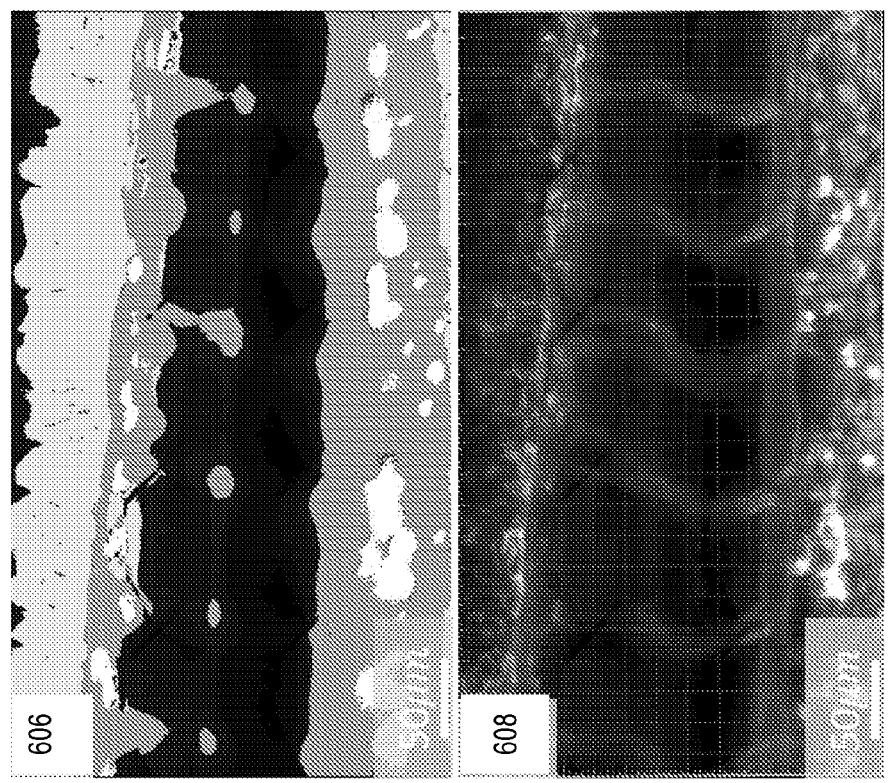
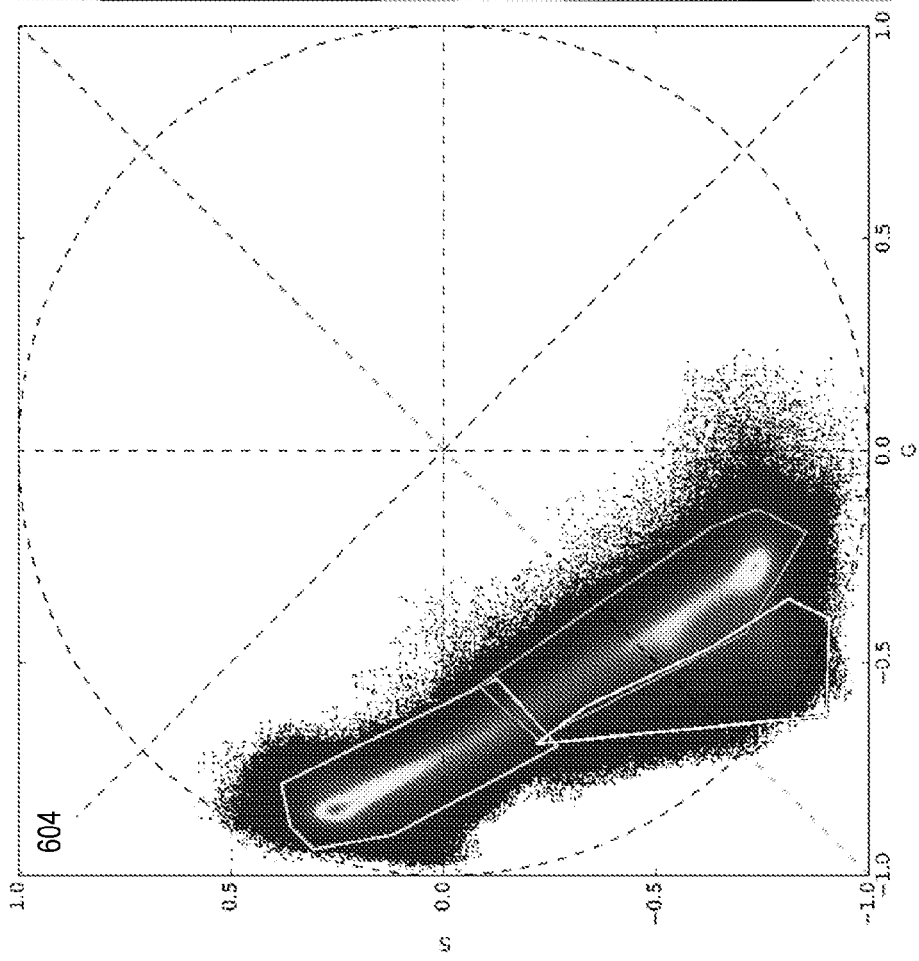
FIG. 6A
FIG. 6B

SEQUENCE LISTING

```
<160> NUMBER OF SEQ ID NOS: 4

<210> SEQ ID NO 1
<211> LENGTH: 60
<212> TYPE: DNA
<213> ORGANISM: Artificial Sequence
<220> FEATURE:
<223> OTHER INFORMATION: synthetic construct

<400> SEQUENCE: 1
ggggacaagt tgtacaaaa aagcaggctt aggccggcca ccatgccaga gccagcgaag        60

<210> SEQ ID NO 2
<211> LENGTH: 43
<212> TYPE: DNA
<213> ORGANISM: Artificial Sequence
<220> FEATURE:
<223> OTHER INFORMATION: synthetic construct

<400> SEQUENCE: 2
ccatggtggc gcgcccctta gcgctggtgt acttggtgat ggc                        43

<210> SEQ ID NO 3
<211> LENGTH: 38
<212> TYPE: DNA
<213> ORGANISM: Artificial Sequence
<220> FEATURE:
<223> OTHER INFORMATION: synthetic construct

<400> SEQUENCE: 3
ctaaggggcg cgccaccatg gcgcgtaagg tcgatctc                              38

<210> SEQ ID NO 4
<211> LENGTH: 56
<212> TYPE: DNA
<213> ORGANISM: Artificial Sequence
```

```
<220> FEATURE:
<223> OTHER INFORMATION: synthetic construct

<400> SEQUENCE: 4
ggggaccact ttgtacaaga aagctgggtt tacgtattag cgttggtggt gggcgg        56
```

HIGH THROUGHPUT SNAPSHOT SPECTRAL ENCODING DEVICE FOR FLUORESCENCE SPECTRAL MICROSCOPY

CROSS REFERENCE TO RELATED APPLICATIONS

This application is a National Phase of International Application No. PCT/US2021/022232, filed Mar. 12, 2021, which designated the U.S. and that International Application was published under PCT Article 21(2) in English, which claims priority to and benefit of U.S. provisional patent application No. 62/989,493, filed Mar. 13, 2020, the entirety of which is hereby incorporated by reference.

STATEMENT REGARDING FEDERALLY SPONSORED RESEARCH OR DEVELOPMENT

This invention was made with government support under Grant No. W81XWH-16-1-0253 awarded by the Medical Research and Development Command. The government has certain rights in the invention.

FIELD

The present description generally relates to systems and methods for spectral fluorescence imaging.

BACKGROUND

The following description includes information that may be useful in understanding the present invention. It is not an admission that any of the information provided herein is prior art or relevant to the presently claimed invention, or that any publication specifically or implicitly referenced is prior art.

Spectral fluorescence imaging can overcome signal overcrowding in molecules, cells and tissues. Multi-color acquisition by multi- or hyperspectral imaging exist in laser scanning or wide-field configurations. The spatial or spectral scanning mechanisms required in the standard configurations limit the imaging speed and efficiency. To improve temporal resolution, snapshot methods have been developed for wide-field microscopes. However, low light throughput still remains an unsolved limitation of multi-color fluorescence microscopy.

SUMMARY

Spectral Fluorescence Imaging (SFI) has been gaining popularity in the life-sciences field because of its multiplexing capability. In this approach, acquisition dimension for each pixel in an image is extended into the spectral domain. This type of detection may be implemented in single point scanning microscopes through a combination of dispersion gratings and detector arrays. However, generally point scanning detection methods have drawbacks of low light efficiency, slow imaging speed and high phototoxicity, complicating their application in multiplexed live imaging with light sensitive samples.

Other approaches for fluorescence snap-shot imaging include Selective Plane Illumination Microscopy (SPIM). SPIM uncouples excitation and detection paths utilizing multiple orthogonally placed objectives and creating a thin sheet of light which reduces unnecessary excitation of fluorophores, photo-bleaching and toxicity. Higher imaging efficiency translates into improved ability of volumetrically imaging large samples at high resolution for extended periods of time. However, the ability to multiplex fluorescent signals in snapshot live microscopy has been limited due to the complexity of acquiring the 3-D spectral dataset (x,y, wavelength) on a 2-D camera sensor. Most SPIM systems sequentially acquire multiple fluorescent signals or optical sections with band-pass filters. Sequential imaging limits temporal resolution and increases phototoxicity, as acquisition time and light dose increase with every additional color.

In some approaches, image mapping spectrometry (IMS) along with SPIM can capture spectral datasets utilizing a single snapshot, overcoming the temporal resolution challenge, but still compromising on the light throughput efficiency. The decreased efficiency, combined with the characteristically low intensity fluorescent signals, has limited snapshot approaches diffusion in fluorescence microscopy.

Spectral phasor analysis may be used for processing multi- or hyperspectral fluorescence datasets. Spectral phasors use Sine and Cosine Fourier transforms to transfer high-dimensional spectral information into a 2-D phasor plane, effectively simplifying the high-dimensional multiplexing complexity. Dimension reduction also facilitates noise reduction.

One example approach for spectral phasor analysis is shown in US Patent Application No. 2020/0378830 by Gratton et al. Therein, images are acquired sequentially using two sine/cosine color filters. Signal multiplexing by phasor analysis is applied to the acquired data.

The inventors herein have identified many disadvantages with the above-mentioned scanning approach with filters. As an example, multiple exposures are required with sequential mechanical filter switches, limiting imaging speed and the temporal resolution. Further, the imaging speed is challenging for video speed imaging applications, such multi-color imaging of a zebrafish embryo beating heart, or for large tiled volumetric imaging, such as single-cell resolution sections of tissue. Furthermore, the use of sinusoidal-transmission filters causes fluorescent signal loss due to absorption. As a result, a significant amount of information that may be useful for signal multiplexing and beneficial in high-speed or low SNR conditions is lost.

Some of the above identified disadvantages may be at least partially addressed by an imaging assembly, comprising: a first dichroic mirror; a second dichroic mirror; wherein a first spectral transmittance curve and a first spectral reflectance curve of the first dichroic mirror have sine wave profiles; and wherein a second spectral transmittance curve and a second spectral reflectance curve of the second dichroic mirror have cosine wave profiles. By utilizing the first dichroic mirror and the second dichroic mirror, spectral encoding is integrated with the acquisition process and further, the dichroic mirrors enable simultaneous collection of transmitted and reflected light, which provides spectral information that may be utilized for multiplexing which are otherwise lost in a filter-based approach.

As one example, a spectral encoding device including two sinusoidal dichroic mirrors are utilized as encoding devices. The spectral encoding device projects a plurality of spectrally encoded channels onto a single camera sensor with single-exposure acquisition. For example, each dichroic mirror transmits a portion of fluorescence signal from the sample and thus, generates a transmitted spectrally encoded channel. A remaining portion of the fluorescence signal is reflected, which is also captured by the spectral encoding device, and thus each dichroic mirror also generates a reflected spectrally encoded channel. Thus, when two dichroic mirrors are used, four channels are generated and captured.

The dichroic mirrors optically transform spectral information into Sine and Cosine Fourier coefficients. The reflected anti-Sine and anti-Cosine portion is also recycled and detected, and used as an intensity normalization factor for the phasor components (e.g., sine and cosine intensity images). This approach increases light throughput (e.g., increase above 80% for 5 commonly available fluorophores), thereby increasing detection efficiency, and temporal resolution with reduced phototoxicity. Further, no mechanical switching of filters is required, and all the spectral information is captured by the transmitted and reflected portions simultaneously, which greatly improves temporal resolution, thereby facilitating frame multiplexing during in vivo imaging for capturing cellular dynamics.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 2E shows an overall transmittance efficiency of a spectral encoding device including dichroic mirrors as compared to transmittance efficiency of sinusoidal filters;

FIGS. 6A an 6B show an example phasor plot and resulting unmixed images respectively, according to an embodiment of the disclosure;

Figure 1A:
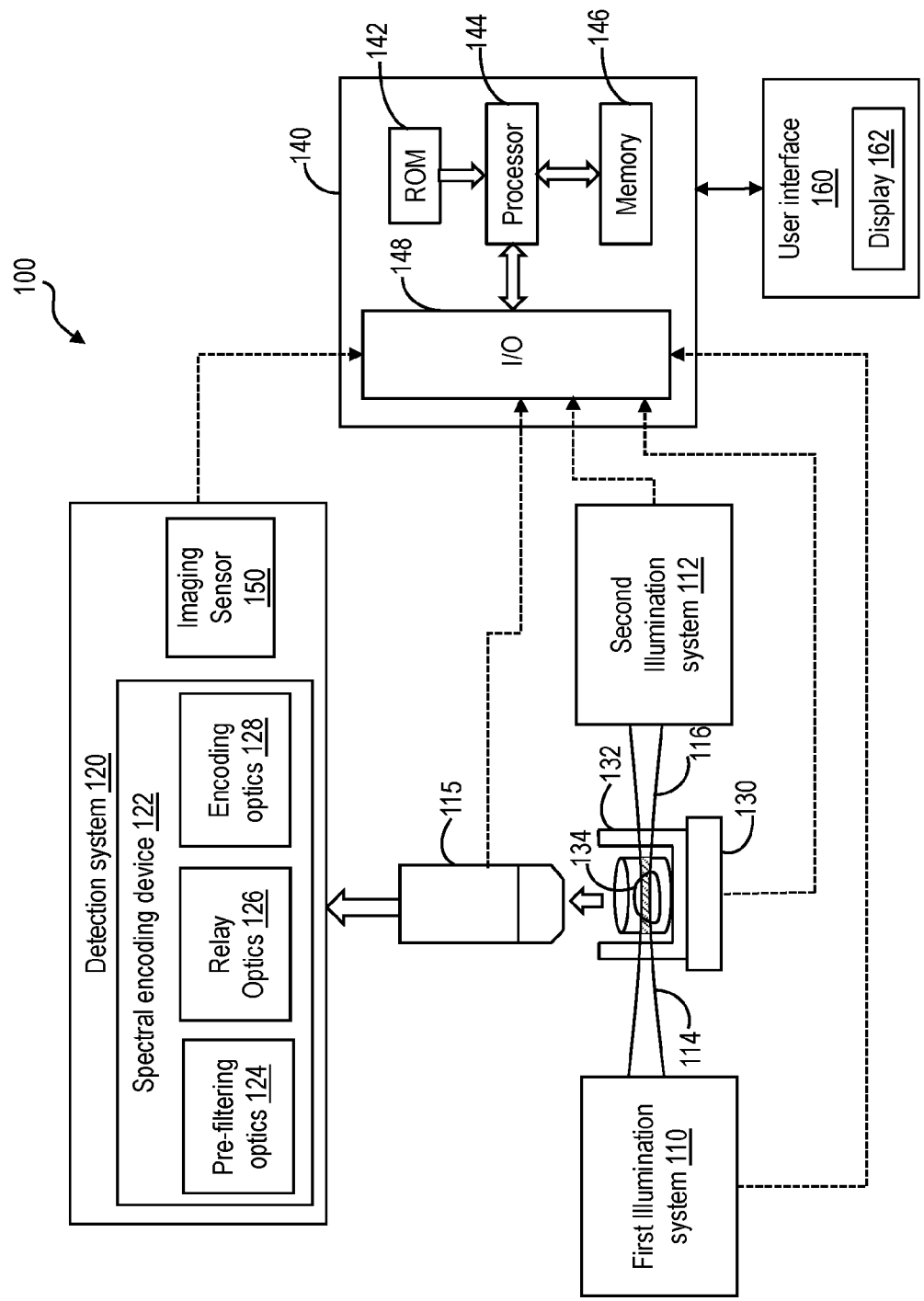
FIG. 1A shows an example overview of a microscope including a spectral encoding device, according to an embodiment of the disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., Revised, J. Wiley & Sons (New York, NY 2006); and Sambrook and Russel, *Molecular Cloning: A Laboratory Manual* $4^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

In some embodiments, properties such as dimensions, shapes, relative positions, and so forth, used to describe and claim certain embodiments of the invention are to be understood as being modified by the term "about." As used herein the term "about" when used in connection with a referenced numeric indication means the referenced numeric indication plus or minus up to 5% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 4%, 3%, 2%, or 1% of that referenced numeric indication, if specifically provided for in the claims.

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

Overview

Figure 1B:
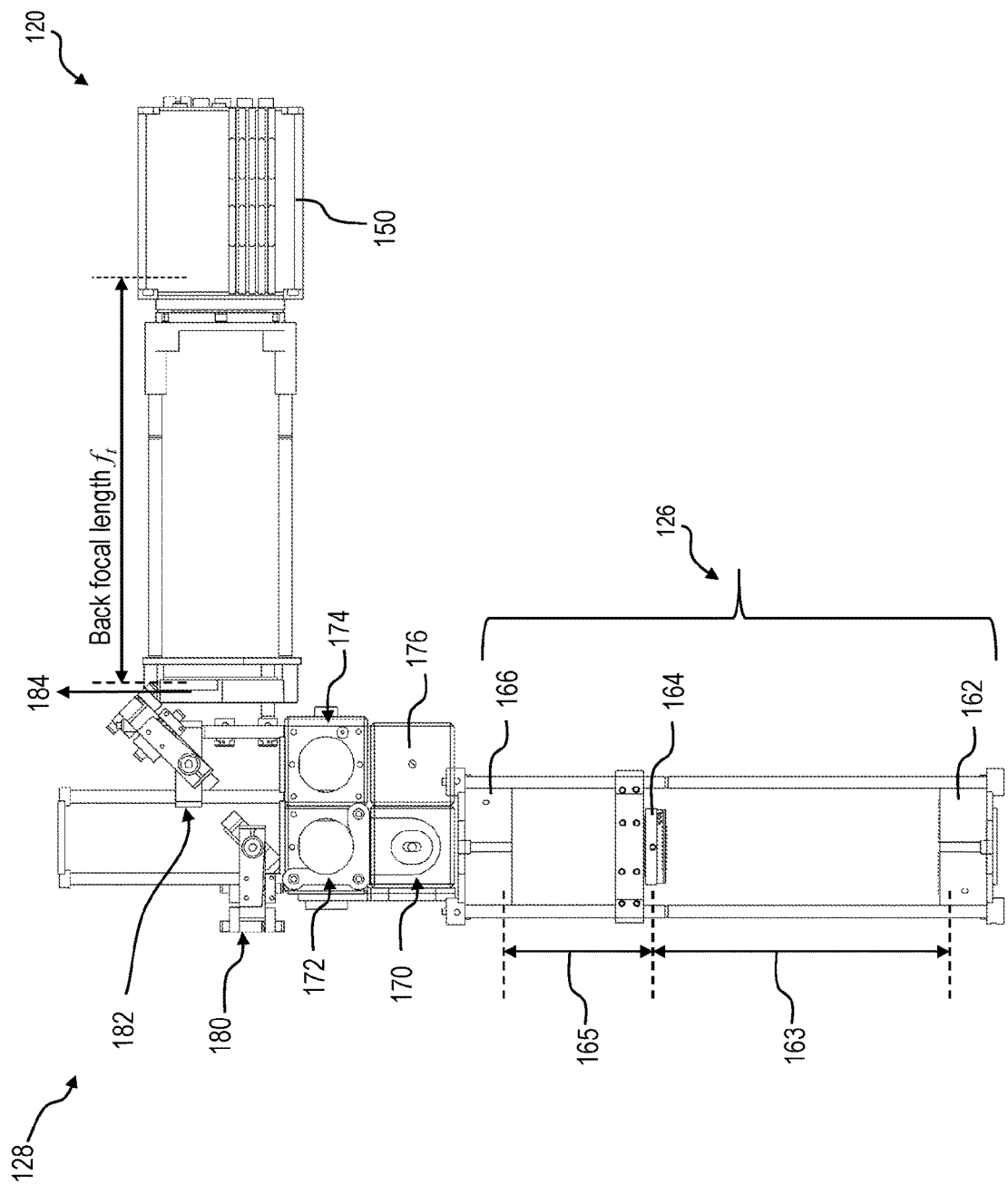
FIG. 1B shows a schematic illustration of a portion of the spectral encoding device of FIG. 1, according to an embodiment of the disclosure.
Figure 2A:
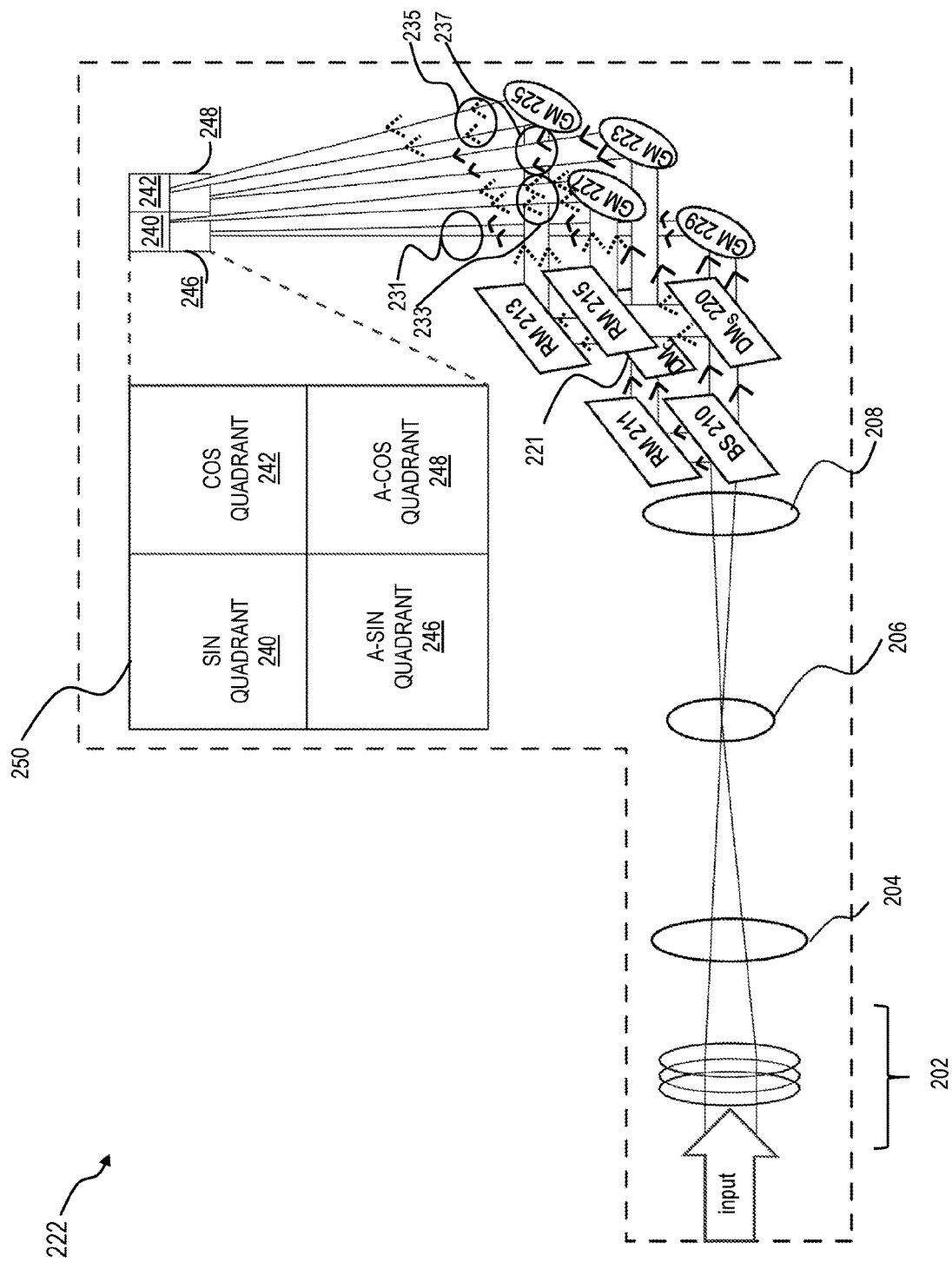
FIG. 2A shows a schematic depiction of optical components of a spectral encoding device, according to an embodiment of the disclosure.
Figure 2B:
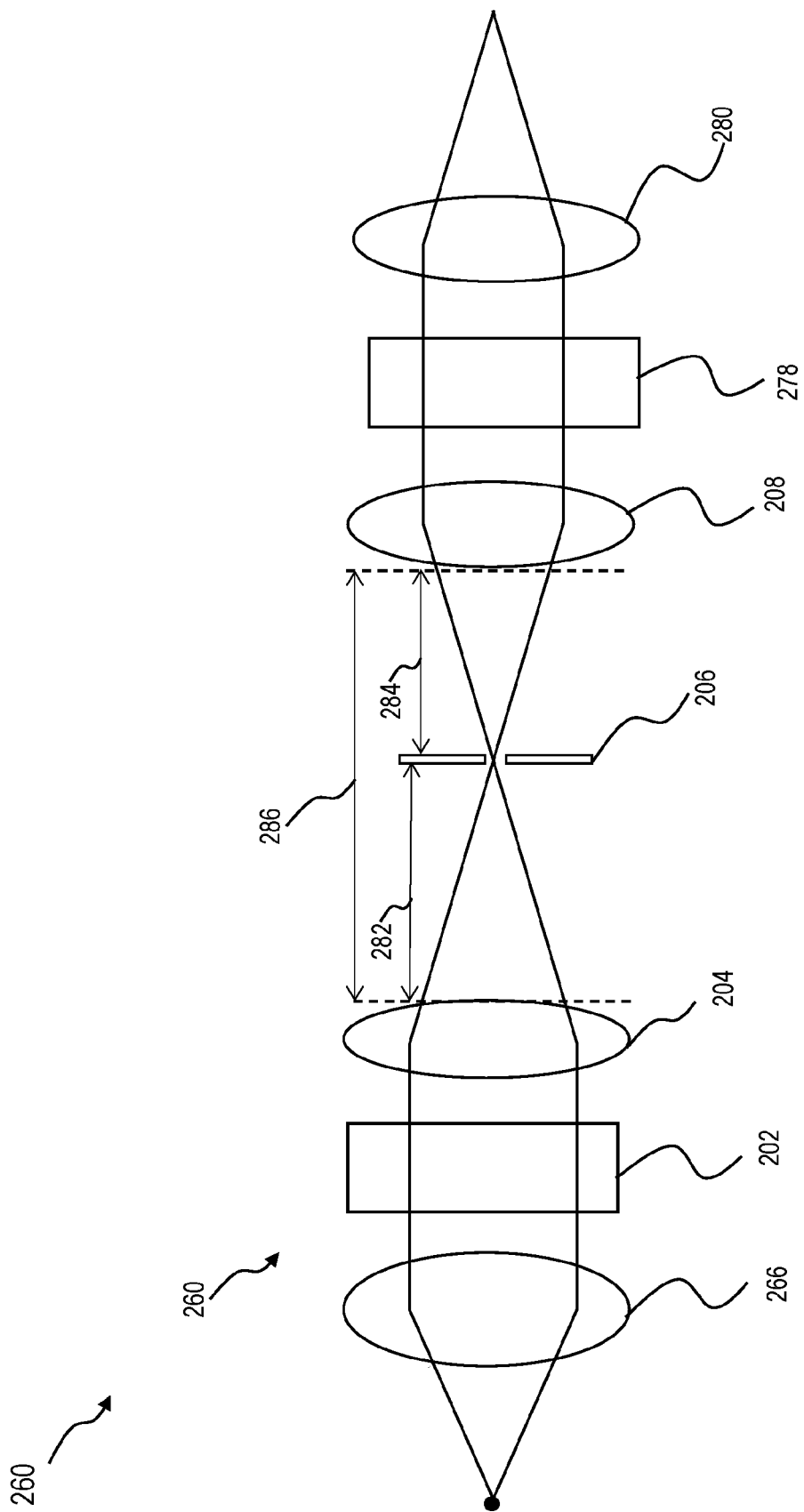
FIG. 2B show a schematic depiction of a simplified optical components of the spectral encoding device of FIG. 2A, according to an embodiment of the disclosure.
Figure 2D:
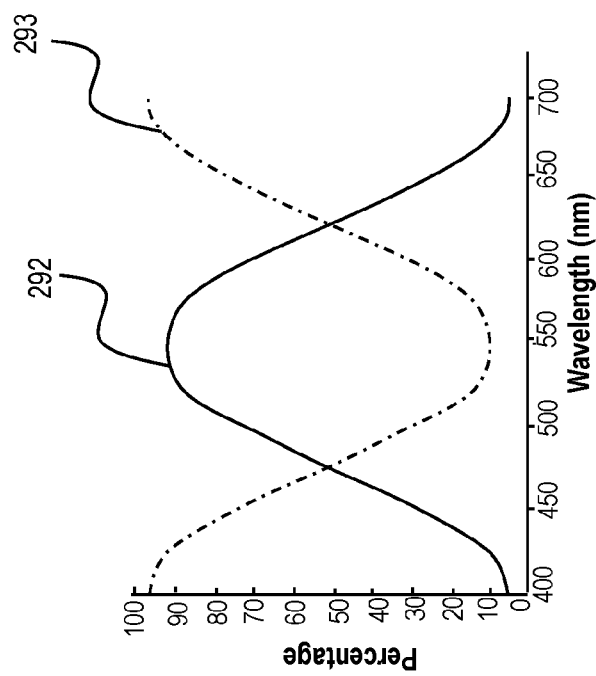
FIGS. 2C and 2D show example graphs of transmittance and reflectance curves of a sine dichroic mirror and a cosine dichroic mirror implemented in a spectral encoding device, according to an embodiment of the disclosure.
Figure 2C:
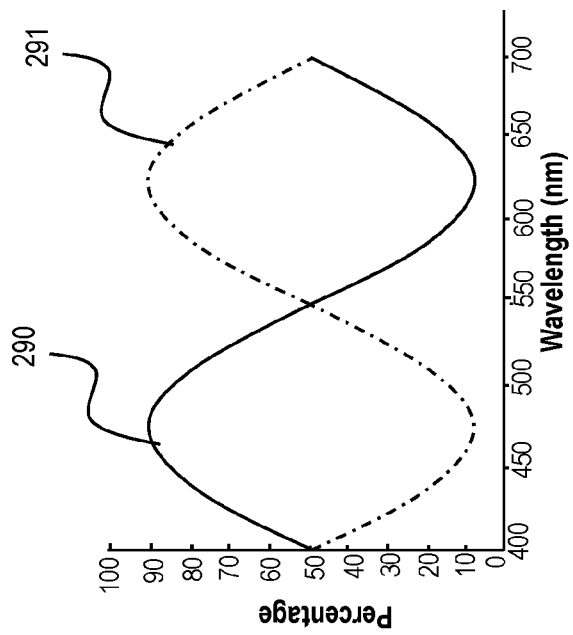
Figure 3A:
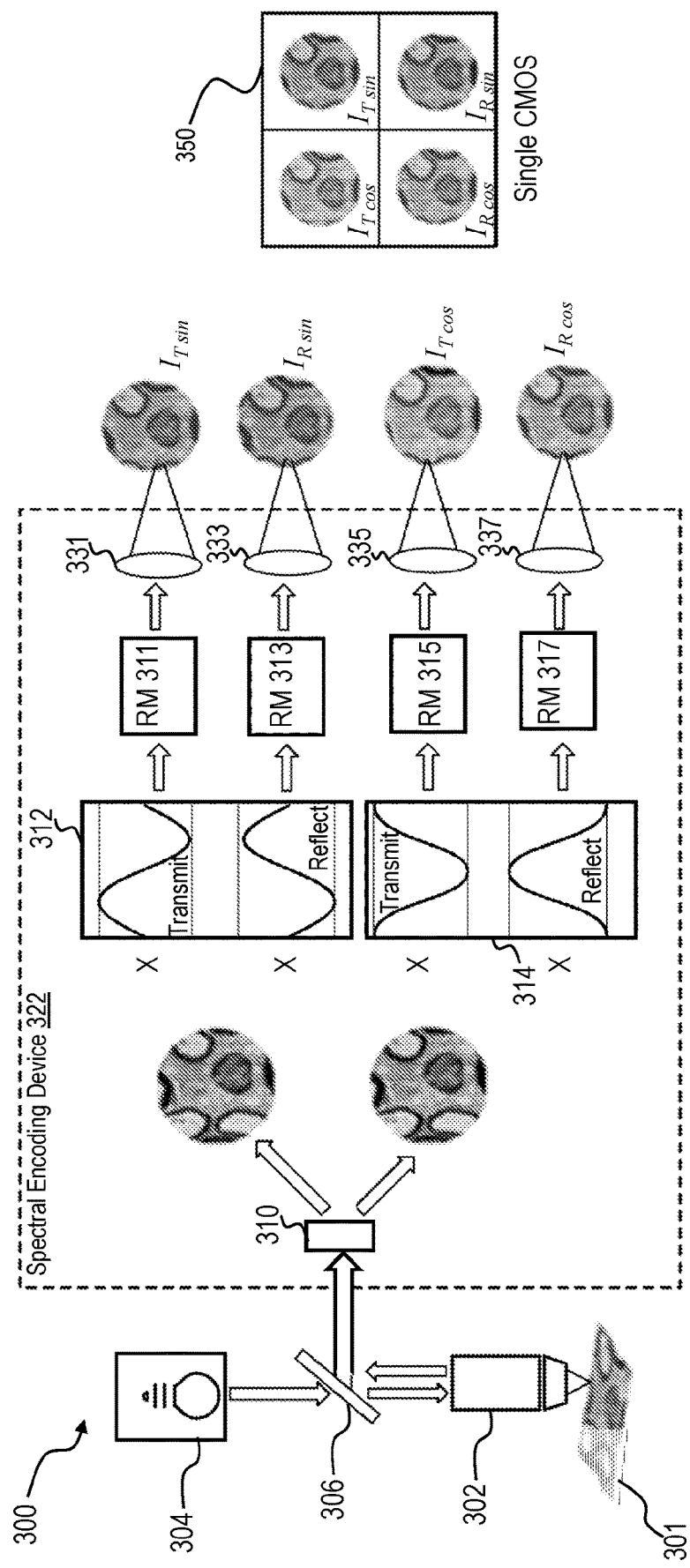
FIGS. 3A, 3B, and 3C show example wide-field, light-sheet, and confocal microscopy implementations of a spectral encoding device, according to an embodiment of the disclosure.
Figure 3B:
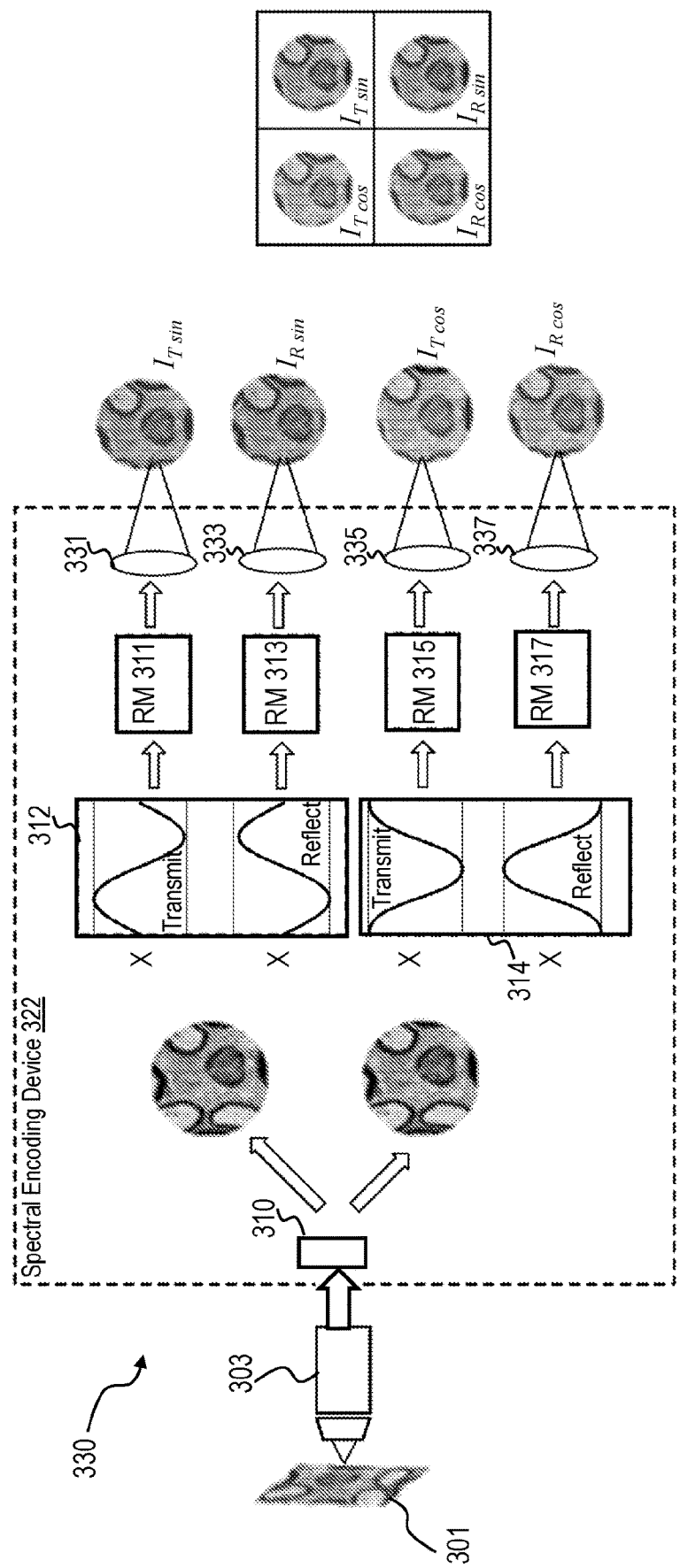
Figure 3C:
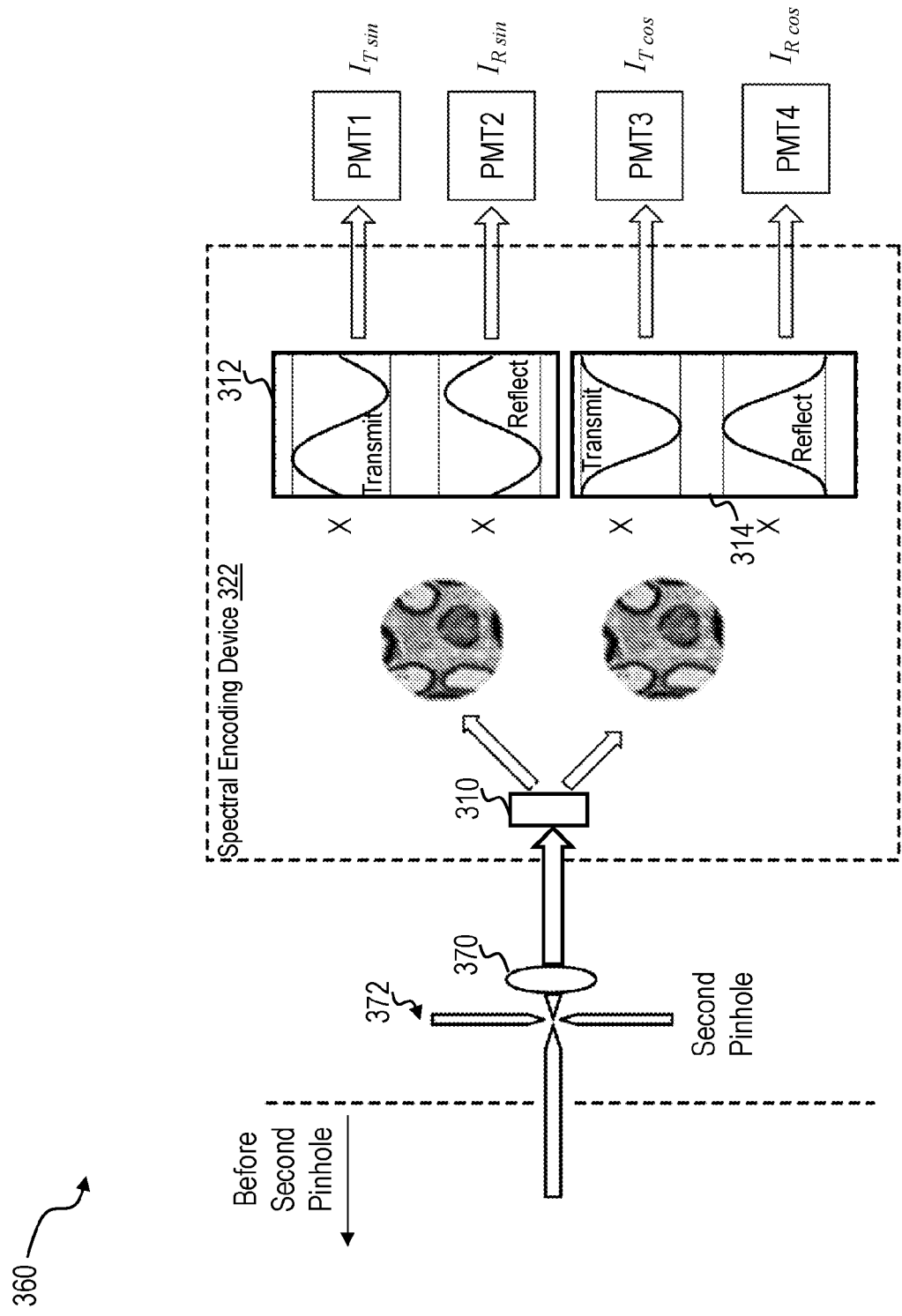
Figure 4A:
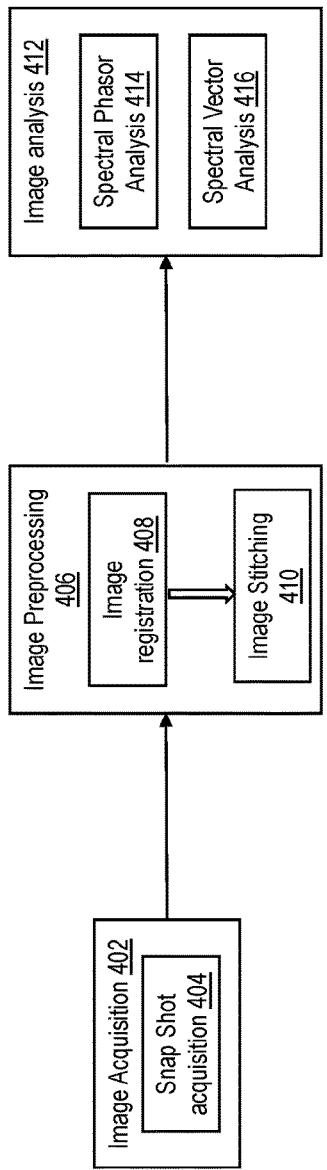
FIG. 4 shows a high-level block diagram of an example image acquisition, image pre-processing, and analysis pipeline for imaging using a spectral encoding device, according to an embodiment of the disclosure.
Figure 4B:
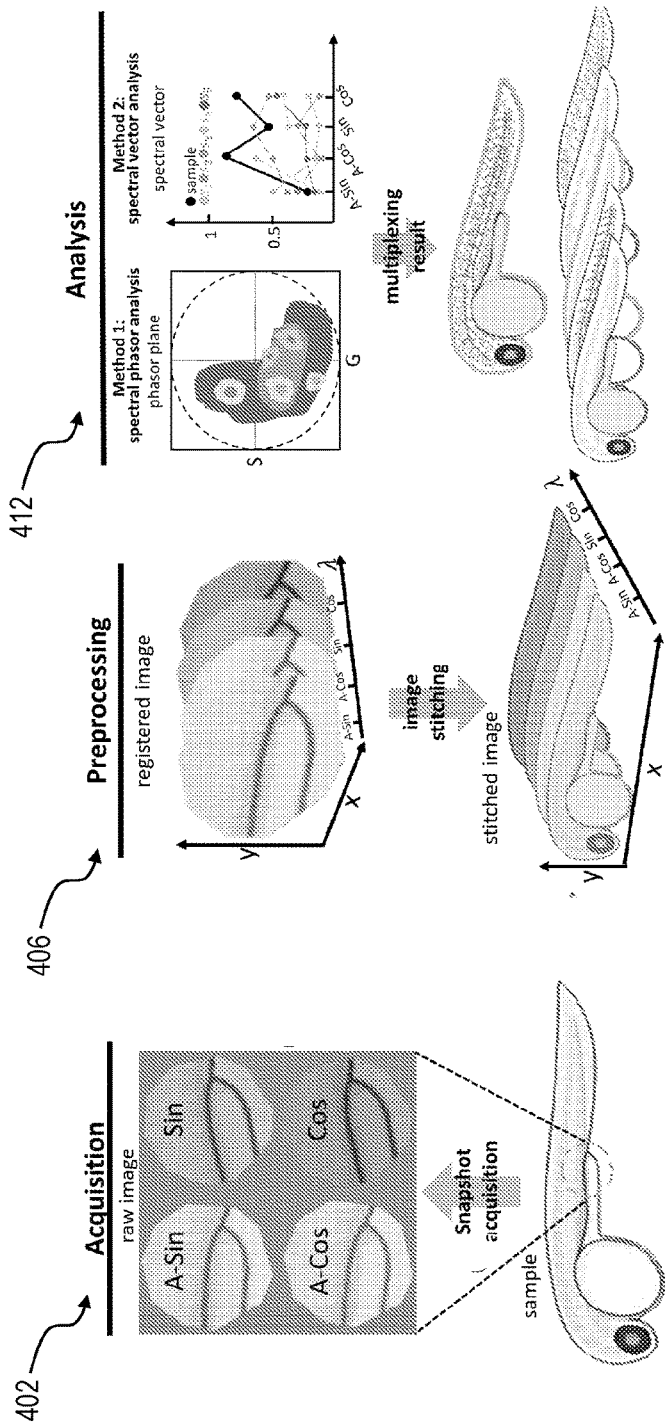
Figure 5:
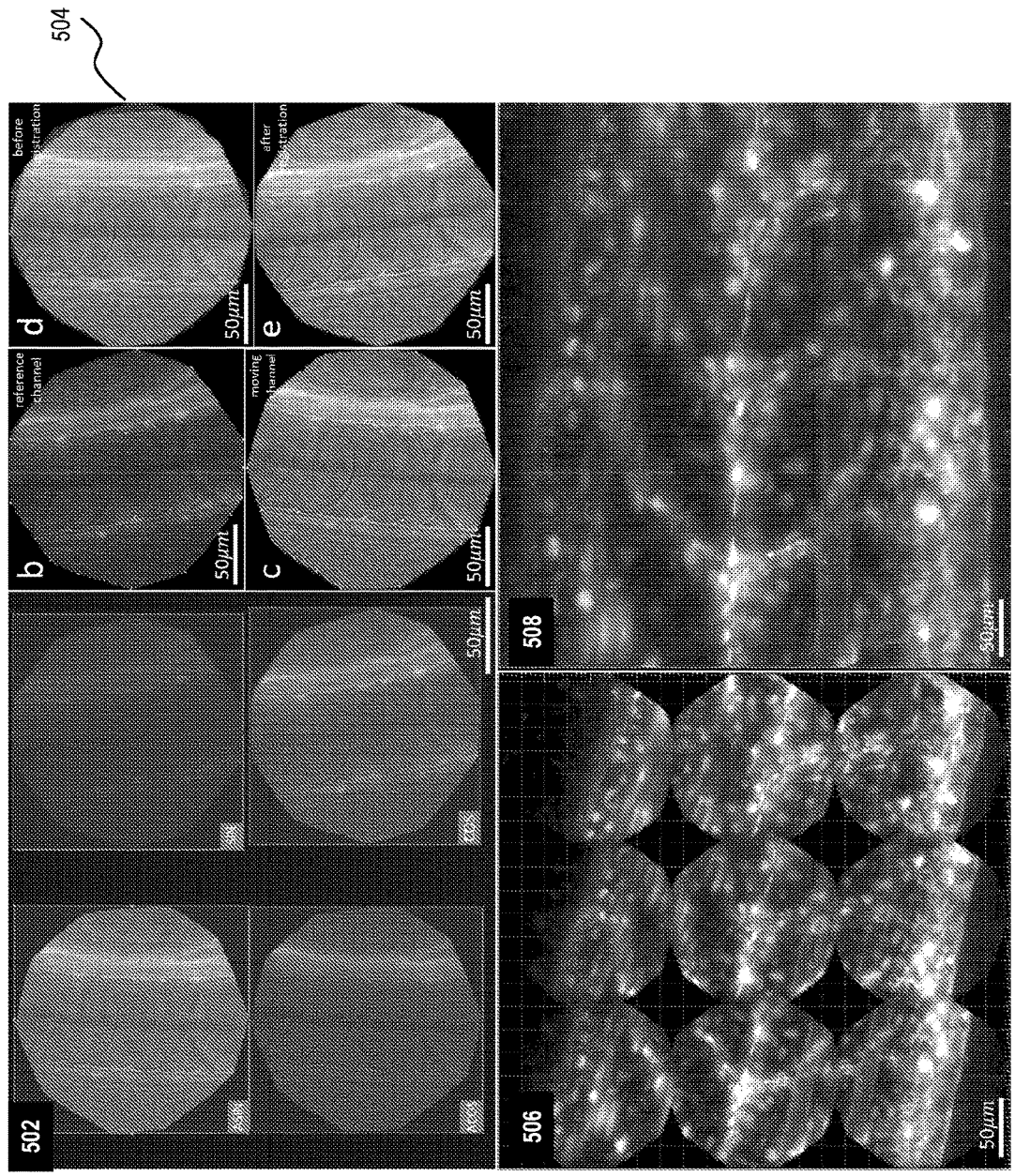
FIG. 5 shows example images during image pre-processing, according to an embodiment of the disclosure.
Figure 7:
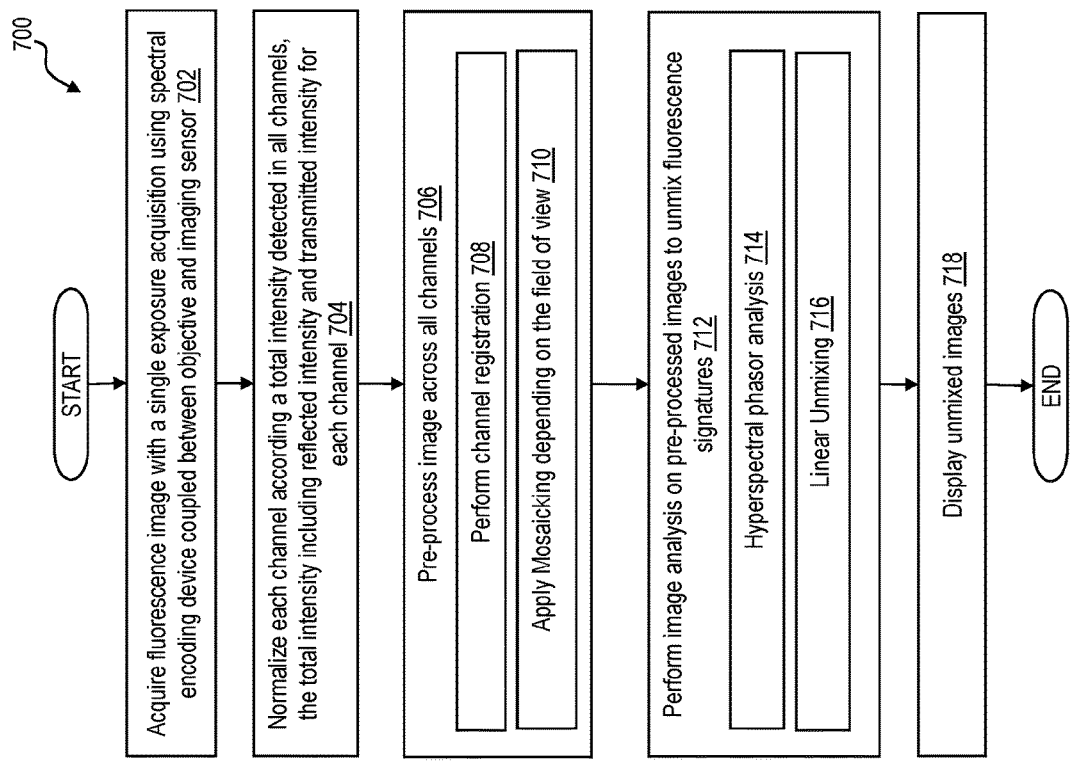
FIG. 7 shows a high-level flow chart illustrating an example method for acquiring and generating multi-spectral or hyper-spectral images utilizing a spectral encoding device, according to an embodiment of the disclosure.
Figure 8:
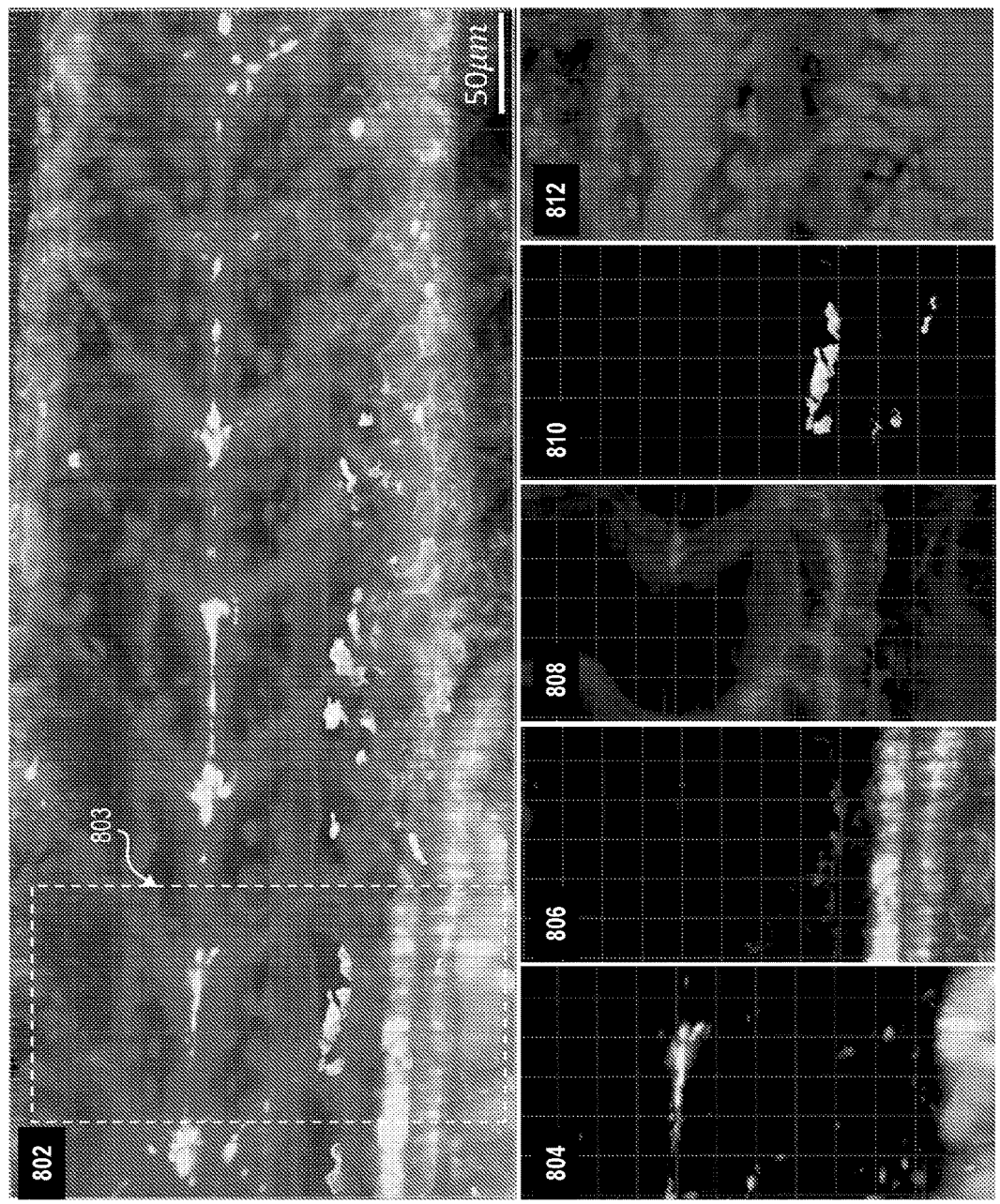
FIG. 8 shows an example tiled volumetric in vivo imaging output utilizing a spectral encoding device, according to an embodiment of the disclosure.
Figure 9:
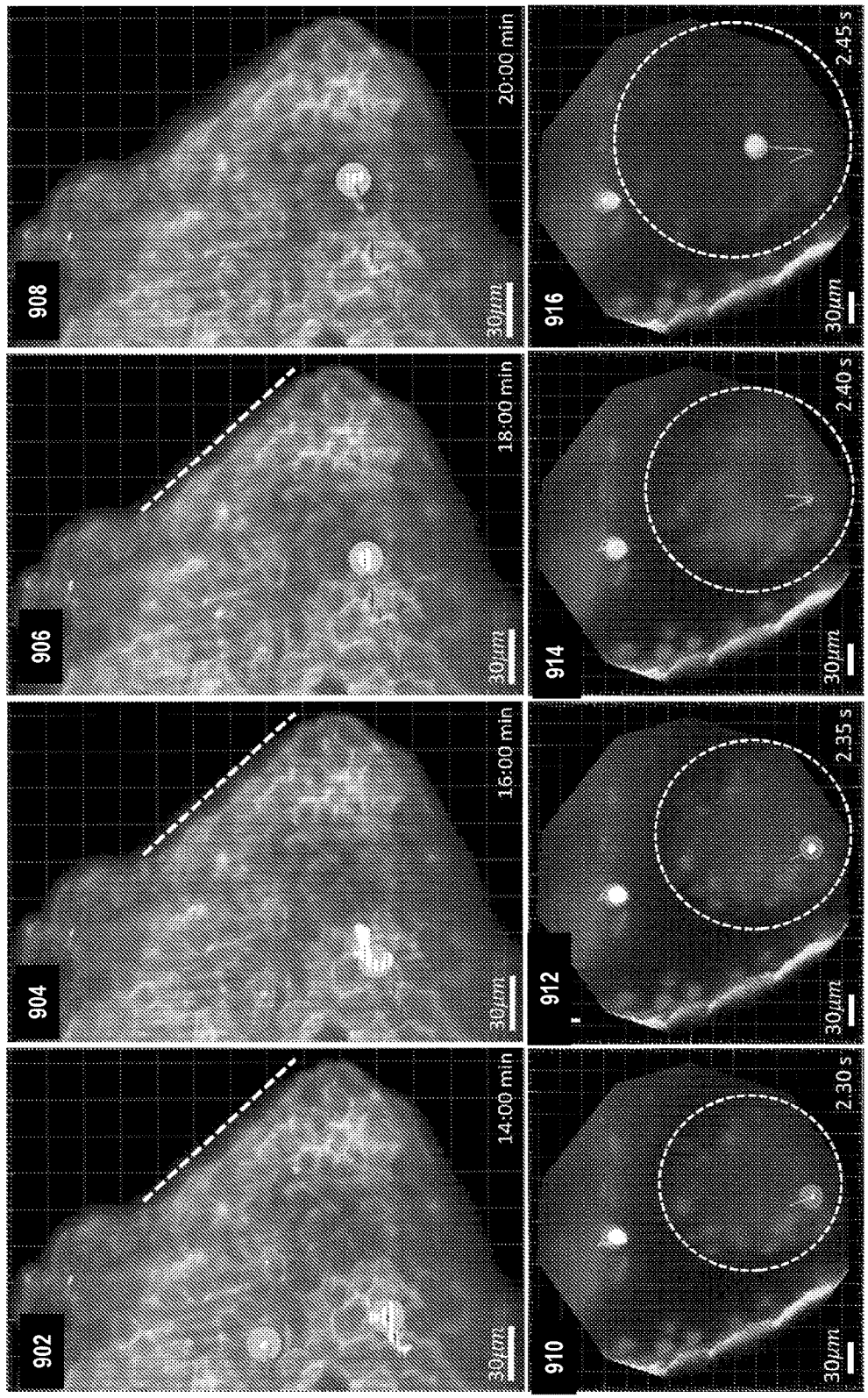
FIG. 9 shows example images acquired during dynamic in-vivo imaging utilizing a spectral encoding device, according to an embodiment of the disclosure.
Figure 10:
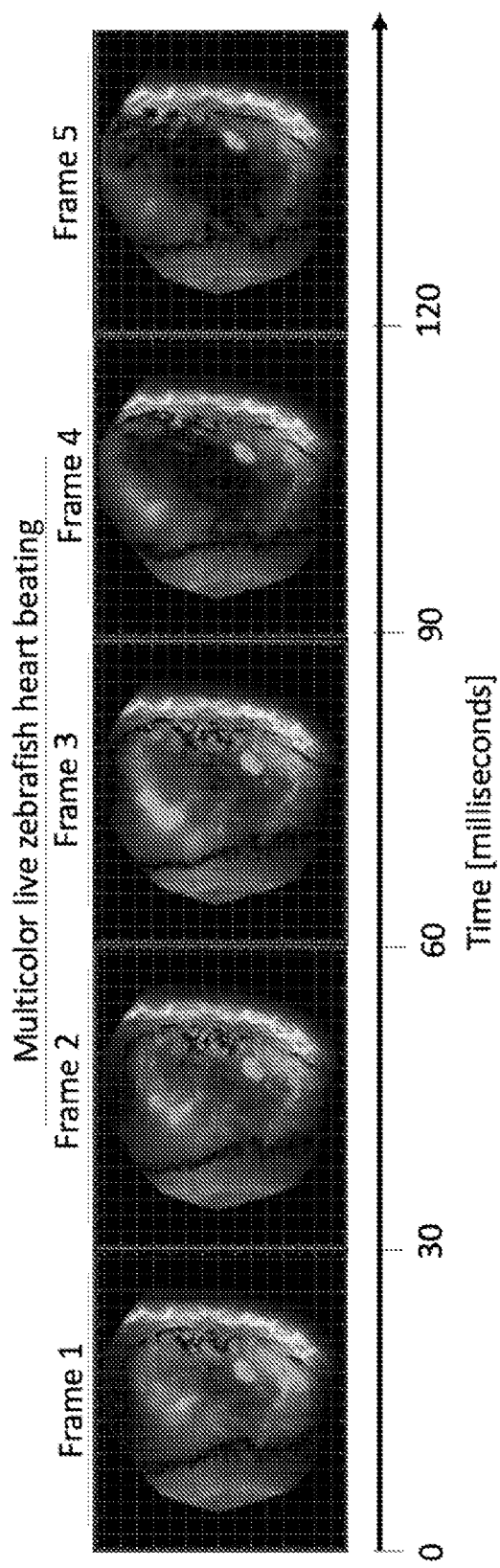
FIG. 10 shows example images acquired during dynamic in-vivo imaging of a live zebrafish heart, according to an embodiment of the disclosure.

The present description relates to systems and methods for multi-spectral and/or hyperspectral fluorescence imaging. In particular, the present description relates to a spectral encoding device that is used for achieving high light throughput and optically encoding fluorescent light signals from a biological sample to sine and cosine Fourier coefficients. In one example, the spectral encoding device includes a sine dichroic mirror and a cosine dichroic mirror, each generating an encoded transmitted light channel and an encoded reflected light channel. All four channels from the two dichroic mirrors are used for intensity normalization, which greatly improves light throughput. Further, the dichroic mirrors have a high transmittance percentage, which improves signal to noise ratio. The spectral encoding device may be integrated with or interfaced with any microscope system. A non-limiting example of a microscope system with which the spectral encoding device may be integrated is shown at FIG. 1A. A schematic illustration of the spectral encoding device is shown at FIG. 1B. Further, example optical components and arrangements of a spectral encoding device are shown at FIGS. 2A and 2B. Example transmittance and reflectance profiles of a sine dichroic mirror and a cosine dichroic mirror that is included in a spectral encoding device is shown at FIGS. 2C and 2D respectively. FIG. 2E illustrates high light throughput efficiency that is achieved with the spectral encoding device for known fluorophores. FIGS. 3A-3C shows example implementations of a spectral encoding device with different microscope systems. FIGS. 4A and 4B schematically and illustratively depict a high level image acquisition, image pre-processing, and image analysis pipeline, during imaging with a microscope system including a spectral encoding device. FIG. 5 shows example images during image pre-processing. FIGS. 6A and 6B show example phasor plot and unmixed image after pre-processing. FIG. 7 shows a high level method for acquiring and generating multi-spectral or hyper-spectral images with a spectral encoding device. FIGS. 8, 9, and 10 show example images acquired during various in vivo imaging via a spectral encoding device.

Technical advantages of an imaging assembly including a sine dichroic mirror and cosine dichroic mirror for spectral encoding include increased light throughput and encoding of high resolution spectral information. A further technical advantage includes improved temporal and spatial resolution due to short acquisition time as mechanical switching is not required and spectral information is captured simultaneously. Further, imaging with the spectral encoding requires a single snap shot acquisition to generate a multi-color spectral image. Additional technical advantages include but not limited to easy integration with existing research imaging devices, easy integration with existing medical imaging devices, easy modification to be an independent imaging device (wide-field), outputs optically processed spectral data, and simplification of post-processing procedure. Taken together, the systems and methods described herein for spectral encoding device with one or more dichroic mirrors provide significant improvement in multi-spectral or hyper-spectral microscopy.

Example Microscope System

FIG. 1 shows a high-level block diagram of an example configuration of a light-sheet microscope 100 used for optical imaging of a biological sample 134 (hereinafter referred to as sample 134 or specimen). The light-sheet microscope 100 is shown as an example microscope system with which a spectral encoding device, alternatively referred to herein as spectral acquisition device, may be integrated or may interface in order to encode spectral information from fluorescence signals. It will be appreciated that the spectral encoding device may be adapted to be utilized with any optical imaging system and its associated imaging sensor without departing from the scope of the disclosure. For example, the spectral encoding system may be utilized with any wide-field microscope, confocal microscope, and/or different types of light-sheet microscope systems.

The microscope 100 includes dual-illumination system comprising a first illumination system 110 and a second illumination system 112 for illuminating the sample from opposite directions. In particular, the sample 134 is illuminated from each side 101 and 102 such that a first light-sheet 114 from the first illumination system 110 and a second light-sheet 116 from the second illumination system 112 pass through the sample illuminating a section or a slice (shown by cross hatching) of the sample 134. For example, the section may be a thin section (e.g., 5-6 μm wide) along the z-axis. Further, the first excitation light-sheet 114 and the second excitation light-sheet 116 may illuminate the specimen 134 such that there is spatial and temporal overlap between the light-sheets 114 and 116. For example, the first light-sheet and the second light-sheet may illuminate a same illumination plane (that is, a plane illuminated by a light-sheet) at the same time for a same time duration. As used herein, a light-sheet refers to a sheet of light generated by an illumination system such that the light-sheet passes through a plane of a sample, thereby illuminating the plane of the sample. The light-sheet is used to optically slice the sample.

Each of the first and second illumination systems 112 and 114 may include a light source 113 and 117 respectively for generating light that is used for forming corresponding light-sheets 114 and 116. The light source may be based at least on a type of excitation provided for light-sheet microscopy, for example linear excitation or non-linear excitation. When, linear excitation is utilized, a signal intensity is proportional to an excitation light intensity. Example implementations of linear excitation include one-photon-excited fluorescence, elastic light scattering, and inelastic light scattering (e.g., Raman or Brillouin). When non-linear excitation is implemented, a signal intensity is proportional to a second (or third) power of an excitation light intensity, in which the sample interacts with two (or three) photons near-simultaneously. Example implementations of non-linear excitation include two-photon-excited fluorescence, second-harmonic generation, three-photon-excited fluorescence, and other higher-order processes. The excitation light-sheets may be created either by a simple cylindrical lens, or by scanning a Gaussian beam, generated via a low NA objective lens, with galvanometer or resonant scanners.

In one example, each of the light sources 113 and 117 may be a laser light source emitting a narrow-band excitation wavelength (e.g., 405 nm, 488 nm, 561 nm, 635 nm, 960 nm, etc.). In some examples, the narrow-band excitation wavelength may be generated by light emitting diodes (LEDs). In another example, the light sources 113 and 117 may be broadband sources (e.g., an incandescent source, an arc source, broad-band LEDs, etc.) generating broad-spectrum light wavelengths. In yet another example, one or more portions of the excitation wavelength may be outside of the visible range. In one example, each light source 113 and 117 may be a same type of light source emitting same excitation light wavelength (e.g., where each light source is a laser light source emitting a desired excitation wavelength, such as 488 nm). In another example, each light source 113 and 117 may be same type of light source but may emit different excitation light wavelengths (e.g., where each light source is a laser light sources but emitting different wavelengths, such as 488 nm and 560 nm). In yet another example, each light source 113 and 117 may be different (e.g., laser and LED).

Each illumination system 110 and 112 further includes illumination optics 115 and 119 for generating corresponding light-sheets 114 and 116. In one example, the light-sheets 114 and/or 116 may be formed statically. Accordingly, the illumination system may include one or more cylindrical lens (not shown) and a low numerical aperture illumination objective (not shown) for focusing the light-sheet on an illumination plane within the sample 134. In another example, the light-sheets 114 and/or 116 may be formed by rapidly scanning a focused illumination beam along the illumination plane. Accordingly, the illumination optics 115 and/or 119 may include one or more galvanometer mirrors (not shown) for generating one or more light-sheets. Further, in some examples, the illumination optics 115 and/or 119 may include one or more beam shaping optics, such as spatial light modulator (SLM), lenses, mirrors, and/or diffraction gratings, for generating desired beam profiles at the illumination plane.

While FIG. 1 shows two illumination systems, in some examples, a single illumination system may be utilized. In some examples, illumination systems 110 and/or 112 may be configured to generate multiple light-sheets, slightly rotated from each other, for multi-directional illumination.

The light-sheet microscope 100 includes a stage 130 comprising a sample holder 132 for mounting the specimen 134. The stage 130 may be an electrically actuated stage movable along the z-axis. The stage 130 may be used to move the specimen 134 along z-axis in order to adjust a position of the light-sheets 114 and 116 within the specimen 134. The movement of the stage 130 may be adjusted by a controller 140. For example, the controller 140 may provide actuation signals to the stage 130 to move the stage along the z-axis.

The light-sheet microscope 100 includes an imaging objective 115 for receiving fluorescence signals from the specimen 134. The imaging objective 115 has an optical axis substantially perpendicular to respective optical axis of the illumination systems 110 and 112. As used herein, substantially perpendicular may account for an error in setting the detection system with respect to the illumination systems and/or a manufacturing error. Further, as used herein, fluorescence signals are emission signals from a specimen, such as specimen 134, resulting from excitation of one or more fluorophores in the specimen. For example, the specimen 134 may include one or more fluorescent labels (e.g., fluorescent labels via fluorescent labelling reagents such as Alexa-488, FITC, etc., fluorescent proteins, such as GFP for green label, mCherry for red label, etc.) that emit fluorescence corresponding to an emission wavelength upon excitation by a light source, that is, light-sheets 114 and 116 in this example. In some examples, the detection system may detect native proteins and/or molecules within the specimen 134 that emit light of specific wavelengths in response to excitation with the light-sheets 114 and 116. Exemplary fluorescent labeling reagents include, but are not limited to, Hydroxycoumarin, Succinimidyl ester, Aminocoumarin, Methoxycoumarin, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorophyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

The light-sheet microscope 100 further comprises a detection system 120 including a spectral encoding device 122 and an imaging sensor 150. The fluorescence signals from the specimen 134 captured by the imaging objective 115 are transmitted to the imaging sensor 150 via the spectral encoding device 122. In particular, the fluorescence signals are encoded by the spectral encoding device 122, and the encoded fluorescence signals (also referred to as encoded emission signals) are captured by the imaging sensor 150. In one example, the imaging sensor 150 is a scientific complementary metal oxide semiconductor sensor (sCMOS sensor). In other examples, depending on the application used, the imaging sensor may be a charge coupled device (CCD) or electron multiplying charge coupled device (EMCCD) or photomultiplier tube (PMT). Further, in one example, the fluorescence signals from the detection system 120 are captured by a single imaging sensor. In some examples, more than one imaging sensor may be used for simultaneously capturing encoded emission signals from one or more channels of the spectral encoding device 122. Details of the spectral encoding device 122 are further described below with respect to FIGS. 1B, 2A-2E, and FIGS. 3A-3C.

The imaging sensor 250 may be communicatively coupled (e.g., via a wired and/or wireless connection) to the controller 140 and image data from the imaging sensor 250 may be processed via the controller 140 and displayed in real-time or near real-time via a display portion 162 of a user interface 160 communicatively coupled to the controller 140.

The controller 140 may include at least one processor (CPU) 144 and memory such as read-only memory ROM 146 and/or random-access memory RAM 142, which comprise computer-readable media that may be operatively coupled to the processor. Thus, one or more of ROM 146 and RAM 142 may include system instructions that, when executed by the processor performs one or more of the operations described herein, such as the process flow of subsequent figures. Processor 144 can receive one or more input signals from various sensory components and can output one or more control signals to the various control components described herein via input/output (I/O) interface 148. In some examples, one or more of the various components of controller 144 can communicate via a data bus. The present example shows an example configuration of the controller 140, it will be appreciated that the controller 140 may be implemented with other configurations.

The controller 140 may provide synchronized control of all opto-mechanical components within the microscope 100. For example, the controller 140 may rapidly perform optical alignment between the light-sheet and the objective on the specimen 134, and enable simultaneous image acquisition with a plurality of detectors (or cameras) within the detection system 120.

The controller 140 may perform image pre-processing according to instructions stored in non-transitory memory, such as ROM 146 and RAM 142. For example, the controller 140 may perform one or more of image registration and stitching on raw images acquired via the imaging sensor 150. Further, the controller 140 may perform image analysis on pre-processed images. For example, the image analysis may be performed according to one or more of a hyperspectral phasor analysis protocol and a linear unmixing protocol, among other image analysis methods. Details of image pre-processing and image analysis is further described below at FIGS. 4A, 4B, 5, 6, and 7.

The spectral encoding device 122 is positioned in a detection light-path between the imaging objective 115 and the imaging sensor 150 of the light-sheet microscope 100. While the present example shows a light-sheet microscope, the detection system 120 may be positioned in a detection light path between an imaging objective and one or more imaging sensors of any microscope system, such as a wide-field microscope, confocal microscope, etc.

The spectral encoding device 122 includes encoding optics 128 for generating one or more encoded light channels. In particular, the encoding device 122 may include one or more dichroic mirrors that are configured to output spectrally encoded light, which are then collected by the imaging sensor 150. In particular, transmitted light and reflected light from each of the one or more dichroic mirrors are collected by the imaging sensor 150. Details of the spectral encoding device 122 are further discussed below. The encoding optics 128 may further include one or more routing mirrors, one or more tube lenses, and/or one or more gimbal mirrors for routing, focusing, and/or angular adjustment of each light channel from the one or more dichroic mirror on to respective portions on the imaging sensor 150.

The spectral encoding device 122 further includes one or more pre-filtering optics 124, and one or more relay optics 126. The one or more pre-filtering optics 124 include one or more long pass filters and short pass filters for filtering out-of-range signals from the fluorescence emission signals from the objective 115, the out-of-range signals including signals that are outside a spectral range of the one or more dichroic mirrors. For example, the one or more pre-filtering optics may be 1, 2, 3, 4 or more long pass filters, and/or 1, 2, 3, 4, or more short pass filters. In one example, the spectral range includes wavelengths in the visible spectrum of light. Further, the one or more pre-filtering optics 124 may include one or more band pass filters for filtering out one or more excitation wavelengths from an illumination light source. For example, a number of band pass filters may be based on a number of excitation wavelengths. That is, as the number of excitation wavelengths increase, the number of band pass filters increases.

The one or more relay optics 126 include one or more relay lenses and a field stop adjustable by a diaphragm for adjusting a field of view of the imaging sensor 150. Details of the spectral encoding device 122 are further discussed below with respect to FIGS. 1B, 2A-2C, and 3A-3C.

Spectral Encoding Device

FIG. 1B shows a schematic illustration of a portion of the detection system 120 including the relay optics 126 and encoding optics 128 portions of the spectral encoding device 122 and the imaging sensor 150. The relay optics 126 include a first relay lens positioned within a first relay lens housing 162, and a second relay lens 166 positioned within a second relay lens housing 166. A field stop is positioned at an intermediate image plane 164 of the first and the second relay lens pair. Further, the intermediate image plane 164 is plane at a back focal length 163 of the first relay lens and a back focal length 165 of the second relay lens.

Positioned downstream of the relay optics 126, in a direction of light path from a sample to the objective to the relay optics 126, is encoding optics 128. The encoding optics 128 include one or more routing mirrors positioned within a roof mirror cube 176, a beam splitter positioned within a beam splitter cube 170, a sine dichroic mirror positioned within a sine dichroic mirror cube 174, and a cosine dichroic mirror positioned within a cosine dichroic mirror cube 172. In various embodiments, each of the sine and cosine dichroic mirror cubes are 1-100 mm, including 1-10 mm, 10-20, 20-30, 30-40, 40-50, 50 or more mm along one dimension of the cube shape.

The beam splitter splits the fluorescence signals from an objective (such as objective 115) equally and direct fluorescence signal towards the sine dichroic mirror and the cosine dichroic mirror (in some examples, at least one routing mirror may route signals from the beam splitter to appropriate dichroic mirror). The sine and cosine dichroic mirrors each transmit a portion of the received fluorescence signal and reflect a remaining portion of the received fluorescence signal. The transmitted and reflected signals from each of the sine and cosine dichroic mirrors are collected and utilized for image acquisition and processing. In this way, an amount of information loss is greatly minimized (~1% loss). As a result, signal to noise ratio (SNR) is greatly improved. Example transmittance and reflectance curves for the sine and cosine mirrors are shown at FIG. 2C. The sine dichroic mirror has sinusoidal transmittance and reflectance curves, thereby generating a sine encoded transmitted light channel and a sine encoded reflected light channel. Similarly, the cosine dichroic mirror has cosine transmittance and reflectance curve, thereby generating a corresponding cosine encoded transmitted light channel and a cosine encoded reflected light channel. Said another way, a first dichroic mirror generates a first spectrally encoded transmitted light portion, and a first spectrally encoded reflected light portion; and a second dichroic mirror generates a second spectrally encoded transmitted light portion and a second spectrally encoded reflected light portion. Further, a respective transmittance and reflectance efficiency for each of the sine and cosine dichroic mirrors are high (for example, greater than 80%). As a result, an amount of signal intensity received from each of the four channels is high, which greatly improves the signal-to-noise ratio. Furthermore, reflected light portions from each of the sine and cosine dichroic mirrors are utilized for normalizing intensity (as further described below), which further improves SNR.

The sine and the cosine mirrors together generate four light channels (two transmitted light portions and two reflected light portions), which are detected at different portions of the imaging sensor 150 or at different imaging sensors. In one example, the gimbal mirrors 180 and 182 direct transmitted and reflected light from each of the four channels towards respective tube lens disposed in a tube lens housing 184. Subsequently, each of the four channels are detected by a respective quadrant of the imaging sensor. An example optical arrangement of the spectral encoding device showing fluorescence signal light path(s) are further elaborated at FIG. 2A.

Turning to FIG. 2A, it shows a schematic illustration depicting an example optical arrangement of a spectral encoding device 222. The spectral encoding device 222 may be an example of the spectral encoding device 122 discussed with respect to FIGS. 1A and 1B. Accordingly, the spectral encoding device 122 is couplable to a microscope, such as microscope 100, and is positioned within an infinity space of the microscope between an imaging objective of the microscope and an imaging sensor 250. The imaging sensor 250 may be an example of imaging sensor 150 discussed at FIGS. 1A and 1B.

The spectral encoding device 222 includes one or more pre-filtering optics 202. The pre-filtering optics 202 may be an example of pre-filtering optics 124 discussed at FIG. 1A. The one or more pre-filtering optics 202 includes one or more of a long-pass filter, a short-pass filter and one or more notch filters. The long-pass and the short-pass filters may be configured to filter out signals that are outside of a spectral range of dichroic mirrors utilized in the spectral encoding device 222. As a non-limiting example, for a set of dichroic mirrors that have a spectral range in the visible spectrum (e.g. 400 nm-700 nm), a 380 nm long-pass filter and a 715 nm short-pass filter may be utilized for removing photons out of the spectral range of the set of dichroic mirrors. Further, the one or more notch filters may be configured to filter out light having excitation wavelength of one or more excitation light sources. As a non-limiting example, a set of notch filters for removing excitation laser light centered at 488 nm, 561 nm and/or 640 nm may be utilized.

As shown, fluorescence emission light (that is, fluorescence signal or simply, fluorescence light) from the imaging objective (indicated as input) passes through the pre-filtering optics 202 and through a relay optics portion comprising of a pair of relay lenses 204 and 208, and a field stop 206. In one non-limiting example, the relay optics may be configured as a Keplerian telescope with a first and a second 50 mm-diameter relay lenses and a field stop. The relay lens 204 creates an intermediate image plane at the field stop 206. In one example, the field stop may be a ring-actuated iris diaphragm. The diaphragm may be adjusted to a size that maximizes the final images formed on the imaging sensor 250 without overlapping. The relay lens 208 then re-collimates the light to infinity space.

An encoding optics portion of the spectral encoding device 222 positioned in the infinity space receive the light rays from the relay optics portion. In particular, fluorescence light from the relay lens 208 is incident on to a beam splitter (BS) 210. In one non-limiting example, the beam splitter 210 may be a 50/50 beam splitter that equally divides the fluorescence emission light into two orthogonal paths, one path directed to a sine dichroic mirror DMs 220 and another path directed to a cosine dichroic mirror DMc 221. The sine and the cosine dichroic mirrors 220 and 221 along with three routing mirrors (RM) RM 211, RM 213, and RM 215 create four spectrally encoded and correlated light paths.

The four spectrally encoded light paths may include a sine encoded transmitted light path comprising transmitted light from the sine dichroic mirror (DM) DMs 220, a sine encoded reflected light path comprising reflected light from the sine dichroic mirror DMs 220, a cosine encoded transmitted light path comprising transmitted light from the cosine dichroic mirror DMc 221, and a cosine encoded reflected light path comprising reflected light from the cosine dichroic mirror DMc 221. The transmitted light paths are shown by solid arrow heads and the reflected light paths are shown by broken arrow heads. Further, gimbal mirrors (GM) GM 229, GM 223, GM 225, and GM 227 are used in front of tube lenses (TL) TL 231, 233, 235, and 237 to adjust an angle of incidence of light from each channel with respect to the imaging sensor 250 from so channel images can be formed on correct quadrants of the imaging sensor 250. As shown, for a four channel generating spectral encoding device 222, the imaging sensor 250 may be partitioned in to four quadrants a sin quadrant 240 receiving transmitted light from the sine dichroic mirror DMs 220, a cos quadrant 242 receiving transmitted light from the cos dichroic mirror DMc 221, an A-sin quadrant 246 receiving reflected light from the sine dichroic mirror DMs 220, and an A-cos quadrant 248 receiving reflected light from the cosine dichroic mirror DMc 221. In this way, each quadrant receives a transmitted or reflected encoded light portion from a dichroic mirror. Thus, for a spectral encoding device including one or more dichroic mirrors and generating N-channels (where each dichroic mirror generates a transmitted encoded light channel and a reflected encoded light channel), an imaging sensor may be partitioned into N non-overlapping portions, where each portion receives encoded light from a corresponding channel. Alternatively, N imaging sensors may be used to image the N-channels. In any case, N number of tube lenses may be used to focus light from the dichroic mirrors and form an N-channel final image on the imaging sensor. In some examples, a focal length of each tube lens may be the same. In one non-limiting example, the focal length of the tube lens may be 175 mm. In various embodiments, each the tube lens may have a focal length of 1-250 mm, including for example 1-25, 25-50, 5-75, 75-100 and 100-250 mm. Further, in order to achieve same magnification across all four channels, the tube lenses may have the same focal length. Thus, in the example shown at FIG. 2A, the tube lenses TL 231, 233, 235, and 237 may each have a same focal length.

Next, FIG. 2B shows a simplified schematic illustration of an optical assembly of the spectral encoding device 222. Similar components are similarly numbered, and explanation of the similarly numbered components will not be repeated for the sake of brevity.

As shown in FIG. 2B, the optical assembly 260 includes an imaging objective 266 (that is, detection objective) of a microscope having a focal length f1. The optical assembly further includes pre-filtering optics 202, first relay lens 204 having a focal length f2, a field stop 206, and a second relay lens 208 having a focal length f3. Further, the optical assembly 260 includes an image splitting component 278 comprising the two dichroic mirrors and routing mirrors that divides and spectrally encodes the emission light into four channels. The optical assembly 260 further includes a tube lens 280 (which may be any of tube lens 231, 233, 235, or 237) for each channel, the tube lens 280 having a focal length f4.

An effective magnification M can be calculated by equation (1).

$$M = \frac{f_2 \cdot f_4}{f_1 \cdot f_3} \tag{1}$$

In order to achieve the same magnification across the four channels, all tube lenses may have the same focal length. In addition, a distance D (indicated by 286) between relay lens 204 and 208 may be adjusted according to the equation (2).

$$D = BFL_1 + BFL_2 \quad (2)$$

where $BFL_1$ (indicated by 282) and $BFL_2$ (indicated by 284) are manufacturer provided back focal lengths for relay lens 204 and 208 respectively. Further, a clear diameter and clear aperture may be utilized in order to accommodate maximum ray angles minimizing vignetting. For example, the estimation may be performed using a back aperture size of the detection objective lens and a maximum angular field of view.

The spectral encoding device 222 optically generates first order Fourier coefficients G(k) and S(k), which may be represented in a 2-D plane called phasor plane. Spectral phasor of a N-channel hyper- or multi-spectral vector is represented by equations (3, 4).

$$G(k) = \frac{\sum_{n=0}^{N-1} I(\lambda_n) \cdot \cos\left(\frac{2\pi}{N} k\lambda\right) * \Delta\lambda}{\sum_{n=0}^{N-1} I(\lambda_n)} \quad (3)$$

$$S(k) = \frac{\sum_{n=0}^{N-1} I(\lambda_n) \cdot \cos\left(\frac{2\pi}{N} k\lambda\right) * \Delta\lambda}{\sum_{n=0}^{N-1} I(\lambda_n)} \quad (4)$$

Where G and S are the real and imaginary coefficients at the k harmonic. $\Delta_n$ represents the wavelength of the n-th spectral channel. $I(\lambda_n)$ denotes the intensity value of the n-th channel. $\Delta\lambda$ is the wavelength band width of a single channel. The denominators in equation (3, 4) represent the integral of the intensity values across all N channels and it's the normalization factor to eliminate the influence of different intensity levels.

The spectral encoding device 222 performs phasor encoding and calculation optically during acquisition. As discussed above, two sinusoidal dichroic mirrors convolve fluorescence emission spectrum by transmitting and reflecting fluorescence emission spectrum. 'SIN' and 'COS' transmitted channels shown in FIG. 2A represent part of the nominators in equations (3,4). 'A-SIN' and 'A-COS' reflected channels are used to estimate total intensity along with 'SIN' and 'COS' for denominator's normalization. G and S are calculated by equations (5,6).

$$G = \frac{C_{ideal}}{I} \quad (5)$$

$$S = \frac{S_{ideal}}{I} \quad (6)$$

$$I = 0.5 * (C + S + AC + AS) \quad (7)$$

$$C_{ideal} = \frac{C - c_C}{a_C} \quad (8)$$

$$S_{ideal} = \frac{S - c_S}{a_S} \quad (9)$$

Where $C_{ideal}$ and $S_{ideal}$ respectively represent the nominators in equation (3, 4). C is the COS channel, S is the SIN channel, AS is the A-SIN channel and AC is the A-COS. I is the intensity value that is used for normalization, accounting for the half total intensity detected in the four channels. $C_{ideal}$ and $S_{ideal}$ can be calculated from equation (8, 9) by applying normalization to the transmittance response profile of the cosine and sine dichroic mirrors. $c_C$ and $C_S$ are respectively the center value of cosine and sine transmittance profiles. $a_C$ and $a_S$ are respectively the amplitude of cosine and sine transmittance profiles. In one non-limiting example, for a given set of cosine and sine dichroic mirrors, the center values and amplitudes are $c_C$=0.52, $c_S$=0.51, $a_C$=0.44 and $a_S$=0.40.

FIGS. 2C and 2D are example graphs showing example transmittance and reflectance profiles of an example sine dichroic mirror, such as sine dichroic mirror DMs 220 at FIG. 2A, and an example cosine dichroic mirror, such as cosine dichroic mirror DMc 221 at FIG. 2A, respectively. The graphs show transmittance/reflectance percentage (that is, percentage of light transmitted/reflected through the dichroic mirror) along the y-axis and a wavelength range from 400 nm to 700 nm along the x-axis.

In particular, trace 290 shows transmittance curve for the sine dichroic mirror, trace 291 shows reflectance curve for the sine dichroic mirror, trace 292 shows transmittance for cosine dichroic mirror, and trace 293 shows reflectance curve for the cosine dichroic mirror. As shown, spectral transmittance for the sine dichroic mirror closely resembles the shape of a sine (FIG. 2C) and a cosine function (FIG. 2D), with a maximum transmittance peaking at 95.8% for sine and at 91.1% for cosine.

As will be further discussed below, the reflected portions of the light signal are also detected and used for normalization of intensity. Due to high transmittance percentage of the sine and cosine dichroic mirrors, combined with the recycling and detection of the reflected light portions by the sine and cosine dichroic mirrors increases light throughput to above 80% for commonly used fluorophores, thereby increasing detection efficiency and with reduced phototoxicity.

An overall transmittance efficiency of a spectral encoding device including a sine dichroic mirror, such as sine dichroic mirror DMs 220, and cosine dichroic mirror, such as cosine dichroic mirror DMc 221, as compared to two sinusoidal transmission filters is shown at FIG. 2E. Specifically, the transmittance efficiency for five commonly utilized fluorophores Cyan Fluorescent Protein (CFP), enhanced Green Fluorescent Protein (eGFP), enhanced Yellow Fluorescent Protein (eYFP), mCherry, and iRFP670, calculated using the two sinusoidal filters (first row, sequential filter) and using the spectral encoding device (second row) are shown. As evidenced by greater overall transmittance efficiency when the spectral encoding device is used, a high light throughput is obtained with the spectral encoding device including the sine and cosine dichroic mirrors and by utilizing the reflected portions in addition to transmitted portions for acquisition and normalization.

Transmittance efficiencies were estimated by taking the realistic loss at each optical surface into consideration. For two-filter approach, the optics include two sinusoidal filters follow by a tube lens, which is estimated using a four-surface doublet achromatic lens. The transmittance profiles are estimated by one period of ideal sine and cosine function with the center value of 0.5 and amplitude of 0.5.

For each fluorophore tested with the spectral encoding device, the overall transmittance efficiency is above 80%, while when sequential filters are applied, the efficiency drops down to as low as 28.3% (for mCherry).

Referring now to FIGS. 3A-3C, they show schematic depictions of a spectral encoding device, such as the spectral encoding device 122 at FIGS. 1A and 1B, or the spectral encoding device 222 at FIG. 2A, implemented in a wide-field microscope, a light sheet microscope (only detection part is shown), and a confocal microscope (only the part after a second pinhole is shown) respectively.

Specifically, FIG. 3A shows a biological sample 301 illuminated by an illumination system 304 in a wide-field microscope system 300. Fluorescence signals from the sample 301 is directed by an excitation dichroic mirror 306 towards a beam splitter 310 of the spectral encoding device 322. Although not shown, the spectral encoding device 322 may include pre-filtering optics and relay optics as discussed above. Each of a sine dichroic mirror 312 and a cosine dichroic mirror 314 receives equal amounts of the fluorescence signal. The sine and cosine dichroic mirrors 312 and 314 generate four spectrally encoded light channels (two transmitted and two reflected light channels), which are then routed by routing mirrors 311, 313, 315, and 317 to tube lenses 331, 333, 335, and 337, respectively. Each tube lens 331, 333, 335, and 337 focus light from each channel on a respective non-overlapping quadrant of an imaging sensor 350. The imaging sensor 350 may be an example of imaging sensor 250 at FIG. 2A, for example.

Next, FIG. 3B shows the spectral encoding device 322 integrated with a light-sheet microscope system 330 comprising a detection objective 303. A detection portion of the light sheet microscope system 330 is show. The light-sheet microscope system 330 may be an example of the light-sheet microscope 100 at FIG. 1A. Similar to FIG. 3A, the sine and cosine dichroic mirrors 312 and 314 generate four encoded light channels, which are imaged by the imaging sensor 350.

FIG. 3C shows a portion 390 of a confocal microscope after a second pin hole 372. The fluorescence signals from objective are passed through a collimating lens 370 before being routed to the beam splitter 310. Further, each of the four channels generated by the sine and cosine mirrors 312 and 314 is detected by a separate photomultiplier tube (PMT).

It will be appreciated the spectral encoding device or the encoding optics portion including at least one sine dichroic mirror and at least one cos dichroic mirror may be positioned in an infinity space between an objective of a microscope and one or more imaging sensors of the microscope.

Acquisition, Image Pre-Processing, and Analysis Pipeline

A block diagram of an example acquisition, image pre-processing, and analysis pipeline is shown at FIG. 4A. An example illustration of the acquisition, image pre-processing, and analysis pipeline is depicted with respect to a biological sample at FIG. 4B. At 402, image acquisition is performed via a microscope, such as microscope 100 at FIG. 1 or any confocal, light-sheet, or wide-field microscopes, using a single snapshot acquisition (indicated at 404). During the acquisition, an integrated spectral encoding device, such as device 122 or 222 or 322, coupled to the microscope generates four channels: sine (encoded and transmitted channel from a sine dichroic mirror), cosine sine (encoded and transmitted channel from a cosine dichroic mirror), anti-sine sine (encoded and reflected channel from a sine dichroic mirror) and anti-cosine 9 sine (encoded and reflected channel from a sine dichroic mirror). Each of the channel images are captured at a corresponding quadrant on an imaging sensor, such as imaging sensor 150, 250 or 350. In this way, raw images from each channel are acquired via the spectral encoding device coupled to the microscope.

Next, at 406, Preprocessing Image registration is applied to the raw images to properly align the raw images from the four encoded channels. In one example, the four channels are aligned using a deformable warping based image registration method. Utilizing a bright-field image, control points of one reference channel and three registering channels may be manually selected and exported (e.g., by using Big Warp plugin function of Fiji which provides visualization of the registered images for evaluating quality of control points). These control points may serve as a basis for a registration transform for the four channels. The parameters of this transform may need to be calculated once and require no change until the optical system is re-aligned or changed. Registration is done by loading raw images and control points previously exported into a MATLAB function. The registered images are then as a 4-channel OME-TIFF phasor cube, with layers corresponding to SIN, COS, A-SIN and A-COS.

The maximum field of view (FOV) of each tile is a hexagon with a pre-determined diameter (e.g., 120 µm). For larger FOV, image tiling may applied during acquisition stage and image stitching may be applied (410) after image registration. For example, image stitching is required, in the case of mosaicked acquisitions. In one non-limiting example, a stitching software (e.g., Imaris Stitcher 9.6 (Bitplane, Switzerland)) may be utilized for stitching. Other stitching protocols may be used and are within the scope of the disclosure. In some examples, tiles may be manually positioned to increase precision in the stitching results.

Next, at 412, image analysis is performed. In one example, a hyperspectral phasor analysis may be performed (414), wherein the four channel images are converted to phasor coefficients G and S, followed by phasor plane analysis. This includes calculating phasor's G and S values through a rapid 2-D matrix pixel-wise multiplication of the four SHy-Cam channels. Spectral signals are then denoised by filtering of the two Fourier components. Representation of the encoded spectral signals as a phasor plot enables graphical selection of regions of interest to explore the multi-color data set. This analysis is performed utilizing HySP—Hyperspectral Phasor software[16]

Alternatively, phasor encoded pixel-wise linear unmixing is performed by treating the four-channel images as spectrally correlated channels across the spectral range (400 nm to 700 nm in this example). Linear unmixing (LU) can be applied directly to the encoded four channels, providing relative contributions for fluorophores in each image pixel.

Taken together, the four channels resulting from spectral encoding device are registered, creating a cube of data with dimensions (x,y,channel), where the channels are sine, cosine, anti-sine and anti-cosine. Mosaicked images are then stitched into larger FOV-volumes for then unmixing through various approaches.

FIG. 5A shows an example of image pre-processing of the raw data from the four channels. In 502, a cropping of the four channels from a bright field image is performed once per alignment in MATLAB. Image shows the camera raw data with four channels distributed in the four quadrants. Next, in image 504, (b) shows a screenshot of 'COS' channel used as the reference channel (e.g., from 'Bigwarp' plugin in Fiji). The reference channel includes manually selected control points. Also in 504, (c) shows a screenshot of 'ASIN' channel, one of the three moving channels, (d) shows an overlay image of 'COS' and 'ASIN' channels before registration with visible misalignment, and (e) shows overlay image of 'COS' and 'ASIN' after registration with well aligned channels. Further, 506 is a screenshot of nine image tiles before stitching. Finally, 508 is a screenshot of stitched image after rotation and crop correction.

Proper registration and alignment of four channels may be required once per optical alignment. As discussed above, image registration is applied to raw images before data analysis. A manual cropping is applied to a target image and the coordinates of the cropping box are exported and saved for future automatic registration. Split-channels are loaded for manually locating control points between three moving channels with one reference. Control points are then saved for further use. Subsequently, a ten-blade adjustable iris as the field stop is used to confine the field of view. These apexes are used as control points. The imaging subject used for capturing registration dataset is one of the biological samples, due to the high number of features. In this example, a zebrafish larvae is imaged. During target image acquisition, a laser excites the fluorescent signal coming from one portion that preferably has distinct shape across the whole field of view. Simultaneously, bright-filed illumination is activated, to capture other textures helpful for control points. The example target images in FIG. 5A contain kdrk: mCherry, labeling vasculature, as well as the surface texture of the zebrafish larvae. The control points only need to be updated when misalignment or physical change occurs.

For mosaicked acquisition, the stitching of multiple tiles may be performed after registration. As the image-cubes contain four channels (ASIN, ACOS, SIN and COS), placement is performed on the one channel that shows the most distinct structures, utilizing the other channels for visual confirmation of the rough alignment. After tiles placement (506), stitching is performed.

Next, FIGS. 6A and 6B show example image analysis using a phasor plot and resulting unmixed image respectively. In one example, spectral analysis and multiplexing can be achieved by applying regions of interest (ROIs) on phasor plane. Alternatively, linear unmixing (LU) can be applied to images acquired via the spectral encoding device as a pixel-wise spectral analysis method for automated ratiometric unmixing results.

FIG. 6A shows the phasor plot of a spectral encoding device image. The sample, a zebrafish embryo Tg (krt4:lyn-EGFP; kdrl:mCherry; lyz:TagRFP), contains three transgenic fluorescent proteins. Polygons ROIs selection on the phasor plane selects corresponding pixels the original image allowing for selective unmixing of signatures. Phasor plot is a 2-D histogram representing the population distribution of phasor coefficients. A higher peak in the phasor plane distribution corresponds to a more frequent spectral signature across all pixels. Each independent spectral signature corresponds to a cluster with large values on phasor plane. However, in the case of a spatially sparse fluorescent signature, the cluster is not strongly distinct. Phasor plot may be viewed in log scale for an easier visualization when different signatures have large difference in spatial sparsity.

Regions selected on the phasor plot highlight the corresponding spatial area in the original data in real time (FIG. 6B, image 606) for reference as a saturated color. An additional overlap is added in the selection ROIs where signal spatial overlapping occurs.

In some examples, Linear Unmixing (LU) may be applied to the pre-processed spectral encoding device images. This requires a set of 4-channel reference spectra, the spectra of pure fluorescent signatures, which were measured under the same imaging conditions used for the final experiment. This step accounts for experimental non-linearities of intensities at different camera exposures, gain and laser excitation power. These reference spectra are provided as a 4 by n array (with n the number of signatures), and solves a pixel-wise linear constrained least square problem utilizing the n reference spectra and the pre-processed images in the shape of four channels (ASIN, ACOS, SIN and COS). The result is the relative contribution of different signatures in each pixel.

FIG. 7 shows a high level flow chart illustrating an example method 700 for acquiring and generating a hyperspectral or multi-spectral image via a spectral encoding device, such as the spectral encoding devices discussed at FIGS. 1A, 1B, 2A-2E, and 3A-3C. The method 700 may be implemented by a controller, such as controller 140, according to instructions stored in non-transitory memory, such as memory 146.

At 702, the method 700 includes acquiring fluorescence image with a single exposure acquisition using spectral encoding device coupled between objective and imaging sensor. During acquisition, the fluorescence signal from a biological sample may be optically split and encoded by one or more dichroic mirrors having a periodic transmittance waveform (e.g., sinusoidal) and a periodic reflectance waveform (e.g., sinusoidal). For example, each dichroic mirror generates a transmitted encoded light channel and a reflected encoded light channel.

At 704, the method 700 includes normalizing each channel according a total intensity detected in all channels, the total intensity including reflected intensity and transmitted intensity for each channel.

At 706, the method 700 includes pre-processing the raw image acquired across all channels. The pre-processing may include performing channel registration 708 and mosaicking 710 depending on a field of view. Examples pre-processing and mosaicking is discussed with respect to FIGS. 5, 6A, and 6B.

Next at 712, the method 700 includes performing image analysis, which may be phasor analysis (step 714) or linear unmixing (step 716). The method 700 further includes displaying the unmixed images. The phasor analysis using images generated from the spectral encoding device can distinguish different species emitting at different wavelengths. Examples of imaging multiple fluorescence signatures are shown below. For example, using 4-channel images, a number of fluorescence signatures may be obtained, wherein the number of fluorescence signatures is less than, equal to, or greater than 4. For example, the number of fluorescence signatures may be 1, 2, 3, 4, 5, 6, 7, 8, 9, 10, or more.

EXAMPLES

FIG. 8 shows an example tiled-volumetric in vivo imaging using light-sheet microscope integrated with a spectral encoding device, such as encoding device 122, 222, or 322. 802 is a maximum intensity projection image showing five unmixed signatures using Phasor Hybrid Unmixing acquired in the trunk area of a 4 dpf transgenic zebrafish embryo with the exposure time of 200 ms. The signals in box 803 are zoomed-in and correspond to cyan—autofluorescence at 804, green—Tg(krt4:GFP) at 806, yellow—Tg(lyz:TagRFP) at 808, magenta—Tg(kdrl:mCherry) at 810, and purple—ubi:H2B-iRFP670 at 812.

FIG. 9 shows SPIM-SHy-Cam dynamic in vivo imaging. Images 902-908 show Zebrafish tail-clip wound healing (dashed line) acquired as a continuous volumetric timelapse with the exposure time of 50 ms. The embryos are labeled in membrane (green) Tg(krt4:GFP), nucleus (purple) ubi: H2B-iRFP670, neutrophil (yellow) Tg(lyz:TagRFP). Neutrophils migration toward the wound can be observed at high-resolution in 3D in the context of tissues and tracked over time. The same embryo's (910-916) beating heart (dashed circles) is captured at 20 frames/second with the exposure time of 50 ms. Neutrophils flowing through cardiac area can be tracked.

Image Acquisition and Sample Preparing

A spectral encoding device prototype was adapted to a home-build light sheet microscope which uses Micro-manager[23] as the acquisition and stage control software. The instrument is equipped with five laser lines and a PCO Edge 5.5 camera (PCO, Gmbh) with resolution 2560 by 2160 pixels. During the testing phase of the spectral encoding device prototype, three laser lines were used to effectively excite the fluorescent signals. A 2×2 binning was applied during image acquisition for an improved signal to noise ratio (SNR).

For multi-color in-vivo imaging tests, Zebrafish embryos that had specific expressions of transgenic fluorescent proteins were collected and raised in a low-salt embryos medium per established procedures until the appropriate time (4 dpf) for imaging. Before imaging, the embryos were immersed in liquid solution of 1% low-melt agarose (made with 30% Danieau solution) and pulled into a glass capillary (5-000-1025, Drummond Wiretrol) with a stainless steel plunger. After the agarose solidified at room temperature (21-23° C.) (1-2 min), the capillary was transferred to the Danieau solution-filled imaging chamber and the agarose containing the embryo was extruded from the micropipettes to have optical access. 0.075% Tricaine was added to both the agarose solution and Danieau solution-filled imaging chamber in order to prevent movement of embryos. During imaging, the imaging chamber temperature was set and kept at 28.5° C.

Image Pre-Processing

A two-step pre-processing is applied to the SHy-Cam images. The first step is registration. The four channels are aligned using a deformable warping based image registration method. Utilizing a brightfield image, control points of one reference channel and three registering channels are manually selected and exported using Big Warp plugin function of Fiji. Big Warp provides visualization of the registered images for evaluating quality of control points. These control points serve as a basis for a registration transform for the four spectral encoding device channels. The parameters of this transform need to be calculated once and require no change until the optical system is re-aligned or changed. Registration is done by loading raw images and control points previously exported into a MATLAB function. The registered images are saved as a 4-channel OME-TIFF phasor cube, with layers corresponding to SIN, COS, A-SIN and A-COS.

The second step is image stitching, in the case of mosaicked acquisitions (FIG. 5). Imaris Stitcher 9.6 (Bitplane, Switzerland) was used as the stitching software for its intuitive and interactive user interface. Due to lack of position metadata for the single 4-channel phasor cubes, tiles were manually positioned to increase precision in the stitching results. Final results were stored in ims format.

Geometrical Unmixing on Phasor Plane

Hyperspectral Phasors software was used for fluorescence signature unmixing and analysis on the 2-D phasor plane. Regions of interest (ROI) were applied to phasor plane to separate multiple signatures (FIG. 6A). Independent signatures were identified by imaging the samples with single fluorescence. Separation locations were identified by visualizing the phasor in logarithmic counts scale and identifying local minima.

Ratiometric Spectral Unmixing

Spectral linear unmixing may be directly applied to the four-channel spectral encoding device intensity images, prior to conversion into G and S spectral phasor coefficients. LU is here treated as a constrained linear least-squares (CLS) problem which can be represented by equation (10).

$$\min_{x^n} \frac{1}{2} \| R^{4 \times n} \cdot x^n - c^4 \|_2^2 \text{ with constraints} \begin{cases} J^n \cdot x^n = 1^n \\ 0^n \leq x^n \leq 1^n \end{cases} \quad (10)$$

where n is the number of fluorescence signatures. $R^{4 \times n}$ is a 4-by-n matrix of reference spectra. Each column of the matrix contains the reference four-channel spectra of a pure spectral signature captured using spectral encoding device under the same imaging condition as the experimental sample with all signature present, maintaining same laser power, exposure time and gain. $x^n$ is the optimal solution of the contribution vector of n different signatures. $c^4 = [AS\ AC\ S\ C]^T$ is the four-channel spectral vector that corresponds to each pixel from the image. $I^n$ is a n-D identity matrix. $J^n$ is a n-D all-ones matrix. $0^n$ and $1^n$ are n-D all-zeros and all-ones vectors. Two constraints are used to better define the problem. The first constraint ensures that all the sum of all contributions equals one. The second confines the range of contributions to be zero to one.

Zebrafish Lines

Lines were raised and maintained following standard literature practice and in accordance with the Guide for the Care and Use of Laboratory Animals provided by the University of Southern California. Fish samples were part of a protocol approved by the IACUC (permit number: 12007 USC). krt4:lyn-egfp and krtt1c19e:lyn-tdtomato transgenic lines were kind gifts from Thomas J. Carney (A*STAR, Singapore). kdrl:mCherry transgenic line was a kind gift from Ching-Ling Lien (Children's Hospital Los Angeles). TgBAC(sox10:BirA-mCherry)ox104a line was used.

mpv17a9/a9;mitfaw2/w2 (casper) line was purchased from Zebrafish International Resource Center (ZIRC) and csf1rj4e1/j4e1 (panther) line was a kind gift from David Parichy (Univ. Virginia). Casper was crossed with panther to produce triple heterozygote mpv17a9/+;mitfaw2/+;csf1rj4e1/+F1 generation fish, which were subsequently incrossed to produce F2 generation with 27 combinations of mutational state of these genes. Since csf1rj4e1 phenotype was not clear in F2 adult with casper phenotype, these fish were outcrossed with panther fish to determine the zygocity of csf1rj4e1 mutation based on the frequency of larva with xanthophores (heterozygote and homozygote produced 50%- and 0%-fraction of xanthophore-positive larva, respectively) by fluorescent microscopy. The casper;csf1rj4e1/j4e1 line is viable and reproducible; either casper;csf1rj4e1/j4e1 line or casper;csf1rj4e1/+ line were outcrossed with other fluorescent transgenic lines over several generations to obtain fish harboring multiple transgenes on casper background either in the presence or absence of xanthophores.

The coding sequences for human Histone 2b region (H2B) and fluorescent protein iRFP670 were amplified from the vector for Tg(PGK1:H2B-chFP)[32] using primers #1 and #2, and piRFP670-N1 (Addgene #45457) using primers #3 and #4, respectively. The PCR products were fused to generate H2B-iRFP670 fusion fragment and cloned into pDONR221 (Thermo Fisher Scientific). Subsequent Multi-Site Gateway reaction was performed using Tol2kit vectors according to developer's manuals. pENTR5'_ubi (Addgene #27320), pDONR221-H2B-iRFP670, and pDONR P2R-P3-WPRE were assembled into pDestTol2pA2 (Tol2kit #394). The resultant pDestTol2-ubi:H2B-iRFP670 was co-injected with tol2 mRNA into one-cell-stage casper zebrafish embryos. Injected F0s were raised and screened for founders. Positive F1s grown to reproductive age were subjected to Splinklette PCR analysis to determine genomic integration sites. Lines showing single copy integrations in unannotated regions determined by Ensembl Zebrafish GRCz11 database were selected and outcrossed with the other transgenic and mutant lines listed above for imaging experiments.

Primer #1 (SEQ ID NO:1): attB1-FseI-H2B-F1: ggggacaagtttgtacaaaaaagcaggcttaggccggccac-catgccagagccagcgaag Primer #2 (SEQ ID NO:2): AscI-H2B-R1: ccatggtggcgcgcccccttagcgctggtgtacttggtgatggc Primer #3 (SEQ ID NO:3): AscI-iRFP670-F1: ctaaggggcgcgccaccatggcgcgtaaggtcgatctc Primer #4 (SEQ ID NO:4): attB2-SnaBI-iRFP-R1: ggggaccactttgtacaagaaagctgggtttacgtatt-agcgttggtggtgggcgg FIG. 9 shows example multicolor snapshot images of live zebrafish heart. 4 days old Zebrafish genetically labeled with epithelial (green), vasculature (magenta) and nuclei (red) were imaged in snapshot multispectral fluorescence at 33 frames per second.

In one implementation, described herein is an imaging assembly including two specially designed dichroic mirrors (DM), wherein a first DM has one harmonic of sinusoidal transmittance curve and an anti-sinusoidal reflectance curve and wherein, the second DM has one harmonic of cosine transmittance curve and an anti-cosine reflectance curve. In various embodiments, the two DMs are each DM cube shapes. In various embodiments, the DM cubes are 1-100 mm, including 1-10 mm, 10-20, 20-30, 30-40, 40-50, 50 or more mm along one dimension of the cube shape. In various embodiments, the assembly includes a beam splitter. In various embodiments, the assembly includes a 50/50 beam splitter cube. In various embodiments, the assembly includes one or more routing mirrors. In various embodiments, the assembly includes 4 routing mirrors. In various embodiments, the assembly includes one or more tube lenses. In various embodiments, the tube lens includes a focal length of 1-250 mm, including for example 1-25, 25-50, 5-75, 75-100 and 100-250 mm. In various embodiments, the assembly includes one or more relay lenses. In various embodiments, the assembly includes a sensor. In various embodiments, the assembly includes an iris. In various embodiments, the assembly includes a roof mirror cube. In various embodiment, the assembly includes two or more gimbal mirror.

Also described herein is a method of using the aforementioned imaging assembly. In various embodiments, the method includes a continuous Fourier Transform (FT). In various embodiments, the FT is a normalized sine and cosine Fourier transform performed at one specific harmonic. In various embodiments, the FT includes:

$$G(k) = \frac{\sum_{i=0}^{N-1} I(i)\cos(\omega i)}{\sum_{i=0}^{N-1} I(i)}, S(k) = \frac{\sum_{i=0}^{N-1} I(i)\sin(\omega i)}{\sum_{i=0}^{N-1} I(i)} \quad (1)$$

$$\omega = \frac{2\pi}{N} \cdot k$$

N: the number of spectral channels
i: spectral channel
k: harmonic number, normally 1,2

In various embodiments, normalization is achieved by utilizing the total intensity of the image. Spectral imaging relies on color information coupled with spatial information to resolve organism properties. It has a trade-off triangle with vertices to be spectral, temporal and spatial resolutions.

The high throughput spectral encoding device described herein is capable of encoding high resolution spectral information, has high light throughput, has minimum compromise on temporal and spatial resolution, and can acquire spectral information with a single image (snapshot acquisition). Further, the high throughput spectral encoding device has synergistic effects including easy integration with existing research imaging devices, easy integration with existing medical imaging devices, easy modification to be an independent imaging device (wide-field), and outputting optically processed spectral data, which simplifies post-processing procedure.

Hyperspectral phasor (HySP) is a Fourier Transform (FT) based computational post-processing method for hyperspectral/spectral image data. It transforms high dimensional spectral data into a 2-D vector consisting of G and S coefficient (1). G and S are respectively the real and imaginary part of the first or second harmonic Fourier coefficient of the original spectral vectors.

By translating HySP calculation into an optical device which can be integrated in the infinity space of existing imaging methods, a continuous Fourier Transform based spectral encoding can be achieved.

The image spectral information is encoded by two dichroic mirrors (DM). The first DM has one harmonic of sinusoidal transmittance curve and an anti-sinusoidal reflectance curve within the spectral range of interest. The second DM has one harmonic of cosine transmittance curve and an anti-cosine reflectance curve within the spectral range of interest.

The light transmitted through the two DMs and then collected by detector/detectors contains the spectral encoded information which can be seen as the first harmonic continuous Fourier coefficients.

The reflected anti-sine and anti-cosine encoded light are also collected by sensors. They are summed with transmitted light to recover the whole emission signal which is later used for normalization.

For the WFM and LSFM applications, only one camera is required to acquired spectral encoded images. For CFM applications, four PMTs are required for encoded spectral signal acquisition.

A special routing mirror array and tube lens array are used in WFM and LSFM applications to route the four split light paths and form images on the same camera sensor.

Case example 1: Hyperspectral snapshot imaging of low signal samples. Current snapshot hyperspectral techniques utilize multiple color-filter deposited on sensors with squared patterns of 4×4 or 5×5 pixels, an extension of the 2×2 pixel Bayer filter (RGGB) commonly used in mobile phone cameras. These filters are designed to reject all light except for a spectral band corresponding to 1/16th (for 4×4) or 1/25th (for 5×5) of the total spectral range acquired. Limitations:

In this process 15/16th (4×4 pattern), or 24/25th (for 5×5 pattern) of the light are rejected and lost. This translates to 93.7% and 96% loss in collecting light. With such low efficiency, utilizing this type of snapshot hyperspectral cameras with fluorescent samples is extremely difficult, as these signals are characterized by a generally low signal to noise.

The spectral encoding device described herein has an estimate loss in light collection of 10%, providing up to 9.6 times lower loss of light and up to 22 fold higher efficiency of signal acquisition. The increased efficiency allows hyperspectral imaging of fluorescent signals.

The final resolution of the image is 4- or 5-fold lower than the resolution of the camera sensor. For example, a 2000×2000 pixels camera will produce a 500×500 pixel image for 4×4, or 400×400 pixel image for 5×5. The spectral encoding device herein produces images 2-fold lower than the pixel number of the camera sensor, doubling the resolution of the final image.

Case example 2: Fast multiplexed imaging of fluorescence. Imaging and separating multiple fluorescent dyes or proteins inside a 2D or 3D sample has been challenging and limited by two factors: i) absence of snapshot spectral imagers with high sensitivity and ii) spectral overlap (spectral similarity) of the fluorescent signals which leads to bleed-through of information across channels. Standard multi-color samples are generally imaged utilizing high sensitivity cameras paired with a set of sequentially switching light emission filters. For a 3 color fluorescence sample this requires acquisition of 3 images and switching of 3 filters. The spectral overlap has limited how many fluorescent dyes can be used in samples and which types. Usual dyes are well spectrally separated to minimize spectral overlap, example blue, green and red fluorescence. Often images require re-alignment as sample moves between filter-switches. With an 30 ms exposure per image, using very high end and expensive high-speed filter switchers that change filter in 30 ms, a three color image requires 30 ms*3colors+30 ms*3filters=180 ms, or 5.5 (3 color) frames per second (fps). A 4 color frame would require 60 ms more, lowering to 4.2 fps.

The spectral encoding device described herein overcomes both the above-mentioned issues by providing high sensitivity spectrally resolved images. There are no moving parts, it requires one image acquired. It does not utilize spectral-band filters, overcoming overlap and bleed-through issues, allowing for high speed 3 or more color images to be acquired. Utilizing the same 30 ms exposure example above, a 3 color frame requires 30 ms (33 fps), a 4 color frame requires still 30 ms (33 fps) allowing acquisition that is 2*n times faster than standard where n is the number of fluorescent dyes imaged. For example, 3 color fluorescence zebrafish heart is acquired at 33 fps, which is 6 times faster than utilizing band-sequential filters.

Case example 3: Large samples/high throughput multiplexed imaging. Imaging samples with multiple spectral overlapping labels requires extending imaging in the spectral dimension acquiring a spectral cube comprising (x,y, wavelength) dimensions. Current instruments capable of performing this type of imaging are either point or line scanning spectrally resolved confocal fluorescent microscopes. Point scanning acquire one point at a time and spectrally spread the signal over a line of detectors, accessing the spectral dimension. The point is then raster scanned through a matrix of positions to acquire an image. Line scanners spread the information on a 2D camera sensor, with one axis spatial dimension (the line) and the other axis the wavelength. For a 2048×2048×32 spectral cube a point scanning spectral confocal microscope would require 1.5 μs time per pixel, including the raster scanning time this translates in 6.3 seconds per spectral cube. Line scanning fluorescent imaging systems reported in literature [DOI: 10.1038/ncomms8990] can collect 1500 lines/second. For a same-sized spectral cube (2048×2048×32) it requires 1.36 seconds acquisition. The spectral encoding device described herein proposed requires 30 milliseconds, 210-folds faster than point scanning and 45-fold faster than line scanning.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML, page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "controller" on data stored on one or more computer-readable storage devices or received from other sources.

The term "controller" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

In some aspects of the present invention, software is provided to execute the operations relating to the equations and calculations provided herein. The software executing the instructions provided herein may be stored on a non-transitory computer-readable medium, wherein the software performs some or all of the steps of the present invention when executed on a processor or a controller.

Selected Embodiments

Although the above description and the attached claims disclose a number of embodiments of the present invention, other alternative aspects of the invention are disclosed in the following further embodiments.

Embodiment 1. An imaging assembly, comprising: a first dichroic mirror; a second dichroic mirror; wherein a first spectral transmittance curve and a first spectral reflectance curve of the first dichroic mirror have sine wave profiles; and wherein a second spectral transmittance curve and a second spectral reflectance curve of the second dichroic mirror have cosine wave profiles.

Embodiment 2. The imaging assembly of embodiment 1, wherein the first dichroic mirror generates a first spectrally encoded transmitted light portion, and a first spectrally encoded reflected light portion; wherein the second dichroic mirror generates a second spectrally encoded transmitted light portion and a second spectrally encoded reflected light portion; and wherein the first spectrally encoded transmitted light portion, first spectrally encoded reflected light, the second spectrally encoded transmitted light, and the second spectrally encoded reflected light are detected an imaging sensor.

Embodiment 3. The imaging assembly of embodiment 2, wherein the imaging sensor is a cMOS sensor.

Embodiment 4. The imaging assembly of embodiment 1, wherein the first dichroic mirror generates a first spectrally encoded transmitted light portion, and a first spectrally encoded reflected light portion; wherein the second dichroic mirror generates a second spectrally encoded transmitted light portion and a second spectrally encoded reflected light portion; and wherein the first spectrally encoded transmitted light portion is detected via a first detector, the first spectrally encoded reflected light is detected via a second detector, the second spectrally encoded transmitted light is detected via a third detector, and the second spectrally encoded reflected light is detected via a fourth detector.

Embodiment 5. The imaging assembly of embodiment 4, wherein the first, second, third, and fourth detectors are photomultiplier tubes.

Embodiment 6. The imaging assembly of embodiment 1, wherein the first and the second dichroic mirrors each receive fluorescence signals from an imaging objective of a microscope.

Embodiment 7. The imaging assembly of embodiment 1, wherein the microscope is any of a light-sheet microscope, a wide field fluorescence microscope, or a confocal microscope.

Embodiment 8. The imaging assembly of embodiment 1, further comprising at least one first routing mirror positioned to receive a first spectrally encoded transmitted light or a first spectrally encoded reflected light from the first dichroic mirror; and at least one second routing mirror positioned to receive a second spectrally encoded transmitted light or a second spectrally encoded reflected light portion from the second dichroic mirror; and wherein the first and the second dichroic mirrors, and the at least one first and second routing mirrors generate four spectrally encoded light portions, the four spectrally encoded light portions including the first spectrally encoded transmitted light, the first spectrally encoded reflected light, the second spectrally encoded transmitted light, and the second spectrally encoded reflected light.

Embodiment 9. The imaging assembly of embodiment 2, further comprising four tube lenses, each positioned to receive one of the four spectrally encoded light portions and focus corresponding spectrally encoded light portions on to the imaging sensor.

Embodiment 10. The imaging assembly of embodiment 9, further comprising four adjustment mirrors, each positioned to adjust a corresponding angle of each of the spectrally encoded light portions with respect to the imaging sensor such that each of the spectrally encoded light portions are imaged at different quadrants of the imaging sensor.

Embodiment 11. The imaging assembly of embodiment 1, further comprising a beam splitter positioned to receive a fluorescence light signal from an imaging objective of a microscope, the beam splitter configured to split the fluorescence signal equally into a first fluorescence signal and a second fluorescence signal; wherein the first fluorescence signal is directed to the first dichroic mirror, and wherein the second fluorescence signal is directed to the second dichroic mirror.

Embodiment 12. The imaging assembly of embodiment 11, further comprising one or more additional routing mirrors to direct one or more of the first and the second fluorescence signals on to one or more of the first and second dichroic mirrors respectively.

Embodiment 13. The imaging assembly of embodiment 11, further comprising one or more relay lenses positioned between the imaging objective and the beamsplitter.

Embodiment 14. The imaging assembly of embodiment 1, further comprising one or more pre-filtering optics, the one or more pre-filtering optics configured to filter out signals outside spectral ranges of the first and the second dichroic mirrors.

Embodiment 15. The imaging assembly of embodiment 12, further comprising one or more pre-filtering optics, the one or more pre-filtering optics configured to filter out signals outside spectral ranges of the first and the second dichroic mirrors, and/or one or more filters configured to filter out wavelengths corresponding to one or more excitation light sources illuminating a sample imaged via the imaging objective.

Embodiment 16. The imaging assembly of embodiment 1, wherein each of the first and the second dichroic mirrors have a spectral range from 400 nm to 700 nm.

Embodiment 17. A spectral encoding assembly for integration with a microscope, the spectral encoding assembly comprising: an encoding portion configured to encode emission light in to a plurality of encoded light channels, the emission light received from an imaging objective of the microscope; wherein the encoding portion includes at least two dichroic mirrors; and wherein each of the at least two dichroic mirrors generate encoded light having a periodic waveform.

Embodiment 18. The assembly of embodiment 17, wherein the spectral encoding assembly is positioned within infinity space of the microscope and between the imaging objective of the microscope and an imaging sensor.

Embodiment 19. The assembly of embodiment 17, wherein the encoding portion further includes at least one beam splitter for directing emission light equally to the at least two dichroic mirrors.

Embodiment 20. The assembly of embodiment 17, wherein the microscope is any of a light-sheet microscope, a wide field fluorescence microscope, or a confocal microscope.

Embodiment 21. The assembly of embodiment 18, further comprising one tube lens corresponding to each encoded light channel, the one tube lens focusing light from each channel on to a separate portion of the imaging sensor.

Embodiment 22. The assembly of embodiment 21, wherein the encoding portion includes one or more adjustment mirrors for directing each of the plurality of encoded light channels from each of the tube lens on to the separate portions of the imaging sensor.

Embodiment 23. The assembly of embodiment 21, wherein the imaging sensor is a cMOS sensor.

Embodiment 24. The assembly of embodiment 21, further comprising a pair of relay lenses and a ring actuated iris diaphragm at an intermediate image plane of the pair of relay lenses; wherein an opening amount of the ring actuated iris diaphragm is based on an imaging area on the imaging sensor such that respective images from each of the plurality of channels do not overlap.

Embodiment 25. The assembly of embodiment 17, further comprising one or more pre-filtering optics between the imaging objective and the encoding portion, the one or more pre-filtering optics configured to filter out emission signals outside spectral ranges of the at least two dichroic mirrors, and/or one or more filters configured to filter out wavelengths corresponding to one or more excitation light sources illuminating a sample imaged via the imaging objective.

Embodiment 26. The assembly of embodiment 17, further comprising relay optics between the imaging objective and the encoding portion.

Embodiment 27. The assembly of embodiment 17, wherein each of the at least two dichroic mirrors have a spectral range including wavelengths in visible spectrum.

Embodiment 28. The assembly of embodiment 18, wherein the imaging sensor is communicatively coupled to an imaging processor.

Embodiment 29. An imaging system, comprising: an imaging objective acquiring fluorescence signal from a sample; an imaging sensor; and a spectral encoding device positioned between the imaging objective and the imaging sensor; wherein the spectral encoding device includes a first dichroic mirror and a second dichroic mirror; and wherein the spectral encoding device generates four encoded light channels via the first and the second dichroic mirrors, wherein each of the four encoded light channels have a periodic waveform.

Embodiment 30. The imaging system of embodiment 29, wherein the four encoded light channels include a first transmitted light channel and a first reflected light channel from the first dichroic mirror, and a second transmitted light channel and a second reflected light channel from the second dichroic mirror.

Embodiment 31. The imaging system of embodiment 30, further comprising a controller including executable instructions stored in non-transitory memory that when executed cause the controller to: determine a normalization intensity by calculating an integral of intensity values of the four encoded light channels; obtain corresponding channel images, via the imaging sensor, for each of the four encoded light channels; and normalize each corresponding channel image according to the normalization intensity.

Embodiment 32. The imaging system of embodiment 31, wherein the controller includes further executable instructions stored in non-transitory memory that when executed cause the controller to: generate a hyperspectral or multi-spectral image according to each normalized channel image.

Embodiment 33. A method for spectral fluorescence imaging, comprising: receiving, at a spectral encoding device, fluorescence signal from a biological sample; generating, via the spectral encoding device, at least two transmitted light channels and at least two reflected light channels; and imaging, at an imaging sensor, the at least two transmitted light channels and the at least two reflected light channels; wherein the spectral encoding device includes at least two dichroic mirrors, each of the two dichroic mirrors having a transmittance and reflectance profile resembling a periodic waveform.

Embodiment 34. The method of embodiment 33, further comprising: registering the images formed by each of the at least two transmitted light channels and each of the at least two reflected light channels.

Embodiment 35. The method of embodiment 34, further comprising: performing phasor analysis on the registered images to generate a phasor plot; and generating an unmixed image according to the phasor plot.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. An imaging assembly, comprising:
a first dichroic mirror;
a second dichroic mirror;
wherein a first spectral transmittance curve and a first spectral reflectance curve of the first dichroic mirror have sine wave profiles; and
wherein a second spectral transmittance curve and a second spectral reflectance curve of the second dichroic mirror have cosine wave profiles.

2. The imaging assembly of claim 1, wherein the first dichroic mirror generates a first spectrally encoded transmitted light portion, and a first spectrally encoded reflected light portion; wherein the second dichroic mirror generates a second spectrally encoded transmitted light portion and a second spectrally encoded reflected light portion; and wherein the first spectrally encoded transmitted light portion, first spectrally encoded reflected light, the second spectrally encoded transmitted light, and the second spectrally encoded reflected light are detected an imaging sensor.

3. The imaging assembly of claim 2, wherein the imaging sensor is a scientific complementary metal oxide semiconductor sensor (sCMOS sensor).

4. The imaging assembly of claim 2, further comprising four tube lenses, each positioned to receive one of the four spectrally encoded light portions and focus corresponding spectrally encoded light portions on to the imaging sensor.

5. The imaging assembly of claim 4, further comprising four adjustment mirrors, each positioned to adjust a corresponding angle of each of the spectrally encoded light portions with respect to the imaging sensor such that each of the spectrally encoded light portions are imaged at different quadrants of the imaging sensor.

6. The imaging assembly of claim 1, wherein the first dichroic mirror generates a first spectrally encoded transmitted light portion, and a first spectrally encoded reflected light portion; wherein the second dichroic mirror generates a second spectrally encoded transmitted light portion and a second spectrally encoded reflected light portion; and wherein the first spectrally encoded transmitted light portion is detected via a first detector, the first spectrally encoded reflected light is detected via a second detector, the second spectrally encoded transmitted light is detected via a third detector, and the second spectrally encoded reflected light is detected via a fourth detector.

7. The imaging assembly of claim 6, wherein the first, second, third, and fourth detectors are photomultiplier tubes.

8. The imaging assembly of claim 1, wherein the first and the second dichroic mirrors each receive fluorescence signals from an imaging objective of a microscope.

9. The imaging assembly of claim 1, wherein the microscope is any of a light-sheet microscope, a wide field fluorescence microscope, or a confocal microscope.

10. The imaging assembly of claim 1, further comprising at least one first routing mirror positioned to receive a first spectrally encoded transmitted light or a first spectrally encoded reflected light from the first dichroic mirror; and at least one second routing mirror positioned to receive a second spectrally encoded transmitted light or a second spectrally encoded reflected light portion from the second dichroic mirror; and wherein the first and the second dichroic mirrors, and the at least one first and second routing mirrors generate four spectrally encoded light portions, the four spectrally encoded light portions including the first spectrally encoded transmitted light, the first spectrally encoded reflected light, the second spectrally encoded transmitted light, and the second spectrally encoded reflected light.

11. The imaging assembly of claim 1, further comprising a beam splitter positioned to receive a fluorescence light signal from an imaging objective of a microscope, the beam splitter configured to split the fluorescence signal equally into a first fluorescence signal and a second fluorescence signal; wherein the first fluorescence signal is directed to the first dichroic mirror, and wherein the second fluorescence signal is directed to the second dichroic mirror, or further comprising one or more pre-filtering optics, the one or more pre-filtering optics configured to filter out signals outside spectral ranges of the first and the second dichroic mirrors.

12. The imaging assembly of claim 11, further comprising one or more additional routing mirrors to direct one or more of the first and the second fluorescence signals on to one or more of the first and second dichroic mirrors respectively, or further comprising one or more relay lenses positioned between the imaging objective and the beam-splitter.

13. The imaging assembly of claim 12, further comprising one or more pre-filtering optics, the one or more pre-filtering optics configured to filter out signals outside spectral ranges of the first and the second dichroic mirrors, and/or one or more filters configured to filter out wavelengths corresponding to one or more excitation light sources illuminating a sample imaged via the imaging objective.

14. The imaging assembly of claim 1, wherein each of the first and the second dichroic mirrors have a spectral range from 400 nm to 700 nm.

15. A spectral encoding assembly for integration with a microscope, the spectral encoding assembly comprising:
an encoding portion configured to encode emission light in to a plurality of encoded light channels, the emission light received from an imaging objective of the microscope;
wherein the encoding portion includes at least two dichroic mirrors; and
wherein each of the at least two dichroic mirrors generate encoded light having a periodic waveform.

16. The assembly of claim 15, wherein the spectral encoding assembly is positioned within infinity space of the microscope and between the imaging objective of the microscope and an imaging sensor, or wherein the encoding portion further includes at least one beam splitter for directing emission light equally to the at least two dichroic mirrors, or wherein the microscope is any of a light-sheet microscope, a wide field fluorescence microscope, or a confocal microscope.

17. The assembly of claim 16, further comprising one tube lens corresponding to each encoded light channel, the one tube lens focusing light from each channel on to a separate portion of the imaging sensor.

18. The assembly of claim 17, wherein the encoding portion includes one or more adjustment mirrors for directing each of the plurality of encoded light channels from each of the tube lens on to the separate portions of the imaging sensor.

19. The assembly of claim 17, wherein the imaging sensor is a cMOS sensor.

20. The assembly of claim 17, further comprising a pair of relay lenses and a ring actuated iris diaphragm at an intermediate image plane of the pair of relay lenses; wherein an opening amount of the ring actuated iris diaphragm is based on an imaging area on the imaging sensor such that respective images from each of the plurality of channels do not overlap.

21. The assembly of claim 16, wherein the imaging sensor is communicatively coupled to an imaging processor.

22. The assembly of claim 15, further comprising one or more pre-filtering optics between the imaging objective and the encoding portion, the one or more pre-filtering optics configured to filter out emission signals outside spectral ranges of the at least two dichroic mirrors, and/or one or more filters configured to filter out wavelengths corresponding to one or more excitation light sources illuminating a sample imaged via the imaging objective, or further comprising relay optics between the imaging objective and the encoding portion.

23. The assembly of claim 15, wherein each of the at least two dichroic mirrors have a spectral range including wavelengths in visible spectrum.

24. An imaging system, comprising:
an imaging objective acquiring fluorescence signal from a sample;
an imaging sensor; and
a spectral encoding device positioned between the imaging objective and the imaging sensor;
wherein the spectral encoding device includes a first dichroic mirror and a second dichroic mirror; and
wherein the spectral encoding device generates four encoded light channels via the first and the second dichroic mirrors, wherein each of the four encoded light channels have a periodic waveform.

25. The imaging system of claim 24, wherein the four encoded light channels include a first transmitted light channel and a first reflected light channel from the first dichroic mirror, and a second transmitted light channel and a second reflected light channel from the second dichroic mirror.

26. The imaging system of claim 25, further comprising a controller including executable instructions stored in non-transitory memory that when executed cause the controller to:
determine a normalization intensity by calculating an integral of intensity values of the four encoded light channels;
obtain corresponding channel images, via the imaging sensor, for each of the four encoded light channels; and
normalize each corresponding channel image according to the normalization intensity.

27. The imaging system of claim 26, wherein the controller includes further executable instructions stored in non-transitory memory that when executed cause the controller to:
generate a hyper-spectral or multi-spectral image according to each normalized channel image.

28. A method for spectral fluorescence imaging, comprising:
receiving, at a spectral encoding device, fluorescence signal from a biological sample;
generating, via the spectral encoding device, at least two transmitted light channels and at least two reflected light channels; and
imaging, at an imaging sensor, the at least two transmitted light channels and the at least two reflected light channels;
wherein the spectral encoding device includes at least two dichroic mirrors, each of the two dichroic mirrors having a transmittance and reflectance profile resembling a periodic waveform.

29. The method of claim 28, further comprising:
registering the images formed by each of the at least two transmitted light channels and each of the at least two reflected light channels.

30. The method of claim 29, further comprising:
performing phasor analysis on the registered images to generate a phasor plot; and
generating an unmixed image according to the phasor plot.

* * * * *